United States Patent [19]

Honma et al.

[11] Patent Number: 5,409,936

[45] Date of Patent: Apr. 25, 1995

[54] IMIDAZOPYRIDINE DERIVATIVES FOR THE TREATMENT OF HYPERTENSION

[75] Inventors: Yasushi Honma, Ageo; Yasuo Sekine, Kawaguchi; Sumihiro Nomura, Kasukabe; Kazuaki Naito, Chiyoda; Hiroshi Narita, Urawa, all of Japan

[73] Assignee: Tanabe Seiyaku Co., Ltd., Osaka, Japan

[21] Appl. No.: 940,336

[22] Filed: Sep. 3, 1992

[30] Foreign Application Priority Data

Sep. 10, 1991 [JP] Japan .................. 3-308561
Jan. 27, 1992 [JP] Japan .................. 4-053043

[51] Int. Cl.⁶ .................. C07D 471/14; A61K 31/44
[52] U.S. Cl. .................. 514/303; 546/118
[58] Field of Search .................. 546/118; 514/303

[56] References Cited

U.S. PATENT DOCUMENTS

| | | | |
|---|---|---|---|
| 4,812,462 | 3/1989 | Blankley et al. | 546/118 |
| 4,816,463 | 3/1989 | Blankley et al. | 514/293 |
| 5,091,390 | 2/1992 | Ardecky et al. | 514/303 |

FOREIGN PATENT DOCUMENTS

| | | | |
|---|---|---|---|
| A7820191 | 12/1991 | Australia . | |
| 0253310 | 1/1988 | European Pat. Off. . | |
| 0291969 | 11/1988 | European Pat. Off. . | |
| 0400835 | 5/1990 | European Pat. Off. . | |
| 0399731 | 11/1990 | European Pat. Off. | 546/118 |
| 0400974 | 12/1990 | European Pat. Off. . | |
| 0420237 | 4/1991 | European Pat. Off. . | |
| 434038 | 6/1991 | European Pat. Off. . | |
| 0461039 | 12/1991 | European Pat. Off. . | |
| 0468470 | 1/1992 | European Pat. Off. . | |
| WO91/11999 | 8/1991 | WIPO . | |

OTHER PUBLICATIONS

Journal of Heterocyclic Chemistry, vol. 28, pp. 97–108 (1991); S. Klutchko et al.
C. J. Blankley et al, Journal of Medicinal Chemistry; vol. 34, No. 11, (Nov. 1991); pp. 3248–3260.

*Primary Examiner*—Raymond Henley, III
*Assistant Examiner*—Phyllis G. Spivak
*Attorney, Agent, or Firm*—Birch, Stewart, Kolasch & Birch

[57] ABSTRACT

An imidazopyridine derivative is disclosed of the formula [I]:

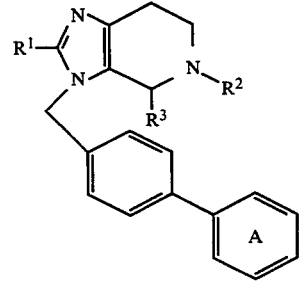

wherein $R^1$ is lower alkyl, $R^2$ is a group of the formula

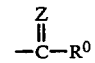

where Z is oxygen atom, $R^0$ is lower alkyl, $R^3$ is carboxyl or lower alkoxycarbonyl and Ring A is tetrazolyl-substituted or unsubstituted phenyl, and pharmaceutically acceptable salt thereof, that are useful in prophylaxis and treatment of hypertension.

10 Claims, No Drawings

IMIDAZOPYRIDINE DERIVATIVES FOR THE TREATMENT OF HYPERTENSION

The present invention relates to novel imidazopyridine derivatives having a hypotensive activity, and processes for preparation thereof.

PRIOR ART

Angiotensin II is a biologically active peptide consisting of eight amino acids, which is produced by specific conversion of angiotensin I by an angiotensin converting enzyme during circulation mainly in the lung. Said angiotensin II constricts vascular smooth muscle as well as promotes the secretion of aldosterone in the adrenal cortex, by which angiotensin II increases blood pressure. Therefore, it is well known that angiotensin II receptor antagonists may be useful in the treatment of hypertension.

Based on the above-mentioned mechanism of action, there have been known some hypotensive agents, for example, 2-n-butyl-4-chloro-5-hydroxymethyl-1-[{2'-(1H-tetrazol-5-yl)biphenyl-4-yl}methyl]imidazole, and the like (cf. European Patent Publication No. 253310A), but these conventional hypotensive agents are all the compounds having a monocyclic nucleus, i.e. imidazole nucleus.

BRIEF DESCRIPTION OF THE INVENTION

An object of the present invention is to provide novel condensed ring-type imidazopyridine derivatives and pharmaceutically acceptable salts thereof, which show potent angiotensin II inhibitory activities and are useful as a hypotensive agent. Another object of the invention is to provide processes for preparing the said imidazopyridine derivatives.

DETAILED DESCRIPTION OF THE INVENTION

The present invention relates to imidazopyridine derivatives of the following formula [I], and pharmaceutically acceptable salts thereof, and further relates to processes for preparing the same.

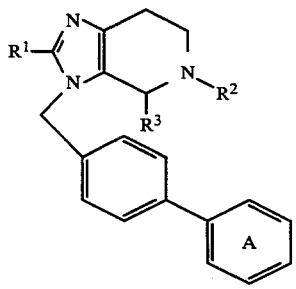

wherein $R^1$ is hydrogen atom or a lower alkyl group; $R^2$ is hydrogen atom, a lower alkylsulfonyl group or a group of the formula:

in which Z is oxygen atom or two hydrogen atoms, and $R^0$ is i) a substituted or unsubstituted lower alkyl group, ii) a lower alkoxy group, iii) a 5- or 6-membered heteromonocyclic group, iv) a substituted or unsubstituted phenyl group, v) hydrogen atom, vi) a substituted or unsubstituted amino group, or vii) a lower alkenyl group; $R^3$ is carboxyl group or a lower alkoxycarbonyl group; and Ring A is a substituted or unsubstituted phenyl group.

Preferred examples of the present compounds [I] are compounds of the formula [I], wherein $R^0$ is i) a lower alkyl group which may optionally be substituted by 1 to 2 groups selected from phenyl group, a halogenophenyl group, carboxyl group, a lower alkoxycarbonyl group, cyanogroup, benzyloxycarbonyl group, a lower alkylthio group, a lower alkylcarbonylamino group, benzoyl group, and a lower alkylcarbonyl group, ii) a lower alkoxy group, iii) a 5- or 6-membered heterocyclic group selected from pyridyl group, furyl group and thienyl group, iv) phenyl group, v) hydrogen atom, vi) a di(lower alkyl)amino group or vii) a lower alkenyl group, and Ring A is a phenyl group substituted by a group selected from a protected or unprotected tetrazolyl group, carboxyl group and a lower alkoxycarbonyl group.

When Ring A is a protected tetrazolyl-substituted phenyl ring, a protecting group for tetrazolyl group includes, for example, trityl group, a tri-lower alkylsilyl group, a cyano-lower alkyl group, a lower alkoxybenzyl group, and the like.

Preferred compounds [I] in view of their excellent pharmacological activity are compounds of the formula [I] wherein $R^1$ is a lower alkyl group; $R^2$ is hydrogen atom, a lower alkylcarbonyl group, a carboxy-lower alkylcarbonyl group, a phenylcarbonyl group or thienylcarbonyl group; $R^3$ is carboxyl group or a lower alkoxycarbonyl group; and Ring A is a phenyl group substituted by a group selected from tetrazolyl group, carboxyl group and a lower alkoxycarbonyl group.

More preferred compounds as a medicament are compounds of the formula [I] wherein $R^1$ is a lower alkyl group; $R^2$ is a lower alkylcarbonyl group; $R^3$ is carboxyl group; and Ring A is a tetrazolyl-substituted phenyl group.

The compounds [I] of the present invention may be used as a medicament either in the form of a free base or a pharmaceutically acceptable salt thereof. The pharmaceutically acceptable salts are, for example, alkali metal salts (e.g. sodium salt, potassium salt, etc.), alkaline earth metal salts (e.g. calcium salt, magnesium salt, etc.), heavy metal salts (e.g. zinc salt, etc.), and organic amine salts (e.g. ammonium salt, triethylamine salt, pyridine salt, ethanolamine salt, a basic amino acid salt, etc.). These salts may easily be prepared by treating the compounds [I] with the corresponding inorganic or organic base in an appropriate solvent.

The compounds [I] of the present invention may exist in the form of two optically active isomers due to an asymmetric carbon atom thereof, and the present invention also includes these optically active isomers and a mixture thereof.

The compounds [I] of the present invention and pharmaceutically acceptable salts thereof may be administered either orally or parenterally and may also be used in the form of a pharmaceutical preparation in admixture with pharmaceutically acceptable excipients suitable for oral administration or parenteral administration. The pharmaceutical preparations may be in solid form such as tablets, capsules, powders, etc., or in liquid form such as solutions, suspensions, emulsions, and the like. When administered parenterally, it may be used in the form of an injection preparation.

The daily dose of the compounds [I] of the present invention and pharmaceutically acceptable salts thereof varies depending on age, weight, conditions of patients and severity of diseases, but when administered orally, it is usually in the range of 0.01 to 10 mg/kg, preferably 0.03 to 5 mg/kg, and when administered parenterally, it is usually in the range of 0.002 to 1 mg/kg, preferably 0.01 to 0.3 mg/kg.

According to the present invention, the compounds [I] can be prepared by reacting a compound of the formula [II]:

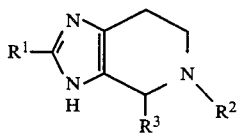

[II]

wherein the symbols are the same as defined above, or a salt thereof with a compound of the formula [III]:

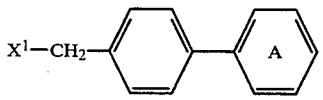

[III]

wherein $X^1$ is a reactive residue, and Ring A is the same as defined above, or a salt thereof.

Among the compounds [I] of the present invention, the compound of the formula [I-a]:

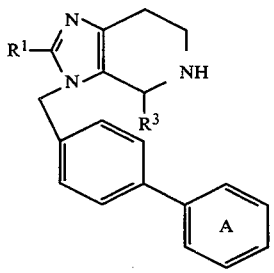

[I-a]

wherein the symbols are the same as defined above, can be prepared by reacting a compound of the formula [IV]:

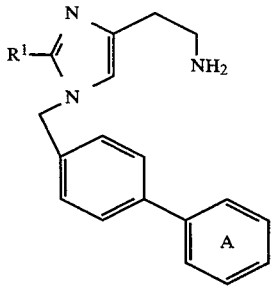

[IV]

wherein the symbols are the same as defined above, or a salt thereof, with a compound of the formula [V]:

$R^3$—CHO     [V]

wherein $R^3$ is the same as defined above, or a salt thereof.

Moreover, the compound of the formula [1-b]:

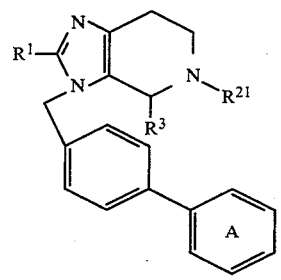

[I-b]

wherein $R^{21}$ is a lower alkylsulfonyl group or a group of the formula:

in which Z is oxygen atom or two hydrogen atoms, and $R^0$ is i) a substituted or unsubstituted lower alkyl group, ii) a lower alkoxy group, iii) a 5- or 6-membered heteromonocyclic group, iv) a substituted or unsubstituted phenyl group, v) hydrogen atom, vi) a substituted or unsubstituted amino group or vii) a lower alkenyl group, and the other symbols are the same as defined above, can be prepared by reacting the compound [1-a] or a salt thereof with a compound [VII:

$X^2$—$R^{21}$     [VII]

wherein $X^2$ is hydroxyl group, and $R^{21}$ is the same as defined above, a salt or a reactive residue thereof.

The reaction between the compound [II] and the compound [III] is carried out in the presence of an alkali metal hydride or an alkali metal alkoxide, or in the presence of an acid acceptor. Suitable examples of the reactive residue ($X^1$) of the compound [III] are, for example, halogen atoms, and the like.

When the reaction is carried out in the presence of an alkali metal hydride or an alkali metal alkoxide, the alkali metal hydride includes, for example, sodium hydride, potassium hydride, etc., and the alkali metal alkoxide includes, for example, sodium methoxide, sodium ethoxide, potassium t-butoxide, and the like. The reaction is preferably carried out in a suitable solvent, under cooling or heating, for example, at a temperature of $-30°$ C. to $50°$ C., more preferably at a temperature of $-10°$ C. to room temperature. The solvent includes, for example, a di-lower alkylformamide, a di-lower alkylsulfoxide, a di-lower alkylacetamide, a lower alkanol, and the like.

When the reaction is carried out in a presence of an acid acceptor, the acid acceptor includes, for example, alkali metal carbonates, and the like. The reaction is carried out in a suitable solvent under cooling or heating, for example, at a temperature of $-10°$ C. to $100°$ C. The solvent includes, for example, acetone, dimethylformamide, dimethylsulfoxide, and the like.

In the reaction, the compounds [I] may be obtained in the form of a mixture of two position isomers, which are produced by reacting the compound [II] with the compound [III] at the 1- or 3-position of the imidazopyridine ring of the compound [II]. In this case, the obtained compounds [I] in the form of a mixture of the position isomers can be separated by a conventional manner such as silica gel column chromatography and recrystallization.

The reaction between the compound [IV] and the compound [V] can be carried out in the presence or absence of an acid or a base. The acid includes, for example, inorganic acids such as hydrochloric acid, sulfuric acid, phosphoric acid, etc., and the base includes, for example, inorganic bases such as alkali metal hydroxides, alkali metal carbonates, alkali metal hydrogen carbonates, and the like. The reaction is carried out in a suitable solvent under cooling or heating, for example, at a temperature of 10° C. to 100° C., preferably at a temperature from room temperature to a boiling point of the solvent to be used. The solvent includes, for example, water, lower alcohols, or tetrahydrofuran, dioxane, or a mixture of water and one of these other solvents.

The reaction between the compound [I-a] and the compound [VI] can be carried out in a conventional manner. For example, the reaction is carried out in the presence of a base or a condensing agent. In the reaction, the compound [VI] may also be used in the form of an acid anhydride thereof, or a reactive derivative thereof, that is, $X^2$ of the compound [VI] is a halogen atom, and the like. Moreover, when $R^{21}$ of the compound [VI] is acetoacetyl, the compound [VI] may be in the form of an anhydride thereof, i.e. diketene.

When the reaction is carried out in the presence of a base, the base may be any conventional ones, and preferably includes, for example, organic bases such as tri-lower alkylamine, pyridine, 4-di-lower alkylaminopyridine, and the like, or inorganic bases such as alkali metal hydrogen carbonates, alkali metal carbonates, alkali metal hydroxides, and the like. The reaction is carried out in a suitable solvent under cooling or heating, for example, at a temperature of −30° C. to 100° C., preferably at a temperature of −10° C. to a boiling point of the solvent to be used. The solvent includes, for example, methylene chloride, chloroform, ethyl acetate, tetrahydrofuran, ether, or a mixture of one of these solvents and water.

When the reaction is carried out in the presence of a condensing agent, the condensing agent includes, for example, dicyclohexylcarbodiimide, 1-ethyl-3-(3-dimethylaminopropyl)carbodiimide, benzotriazol-1-yloxy-tris(dimethylamino)phosphonium hexafluorophosphate, and the like. In addition, a compound such as hydroxybenzotriazole, N-hydroxysuccinimide, etc., may be used as a promoter. The reaction is carried out in a suitable solvent under cooling or heating, for example, at a temperature of −10° C. to 80° C., preferably at room temperature. The solvent includes, for example, methylene chloride, chloroform, di-lower alkylformamide, acetonitrile, tetrahydrofuran, and the like.

The compounds [I] obtained above may, if necessary, be converted to each other, for example, the compound [I] wherein $R^2$ is a carboxy-lower alkylcarbonyl group, i.e. a compound of the formula: [I-e]:

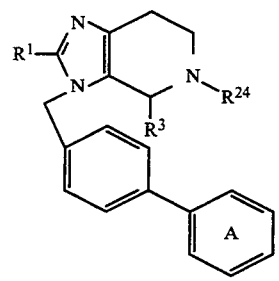

wherein $R^{24}$ is a carboxy-lower atkylcarbonyl group, and the other symbols are the same as defined above, can be prepared by subjecting a compound of the formula [I-d]:

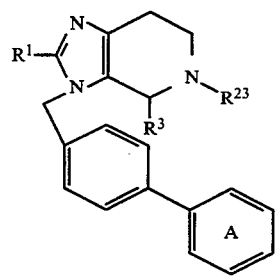

wherein $R^{23}$ is a lower alkoxycarbonyl-lower alkylcarbonyl group, and the other symbols are the same as defined above, or a salt thereof to hydrolysis.

The hydrolysis of the compound [I-d] may be carried out by a conventional manner. For example, the reaction is preferably carried out in a suitable solvent under cooling or heating, for example, at a temperature of 0° C. to 100° C., preferably at a temperature of 20° C. to 50° C., in the presence of a base (e.g. alkali metal hydroxide, etc.). The solvent includes, for example, a lower alkanol, or a mixture of a lower alkanol and water.

In the above mentioned reactions, each starting compound can be used either in the form of a free base or a salt thereof. The salts of the compounds [I-a] and [I-d] are, for example, alkali metal salts, alkaline earth metal salts, heavy metal salts, organic amine salts, inorganic or organic acid salts, and the like. The salts of the compound [II] are, for example, hydrochloride, hydrobromide, oxalate, and the like. The salts of the compound [IV] are, for example, hydrochloride, hydrobromide, oxalate, and the like. The salts of the compound [V] are, for example, alkali metal salts, etc., when $R^3$ is carboxyl group. The salts of the compound [VI] are, for example, hydrochloride, etc., when $R^{21}$ is pyridylcarbonyl group.

When the compound [I] is obtained in the form of a racemic mixture, the racemic compound [I] may easily be optically resolved in a conventional manner.

When the compound [I] is the compound of the formula [I] wherein Ring A is a protected tetarzolyl-substituted phenyl group, a protecting group for said carboxyl group and/or for said tetrazolyl group may easily be removed by a conventional manner.

The starting compound [II] may be prepared by the method disclosed in Japanese Patent First Publication (KOKAI) No. 167687/1986 or Japanese Patent First Publication (KOKAI) No. 101062/1990.

The starting compound [IV] may be prepared by reacting a compound [VII]:

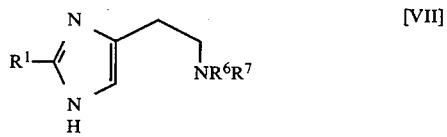

wherein R⁶ and R⁷ are each hydrogen atom or a protecting group for amino group, and R¹ is the same as defined above, with the compound [III] under the same conditions as the reaction between the compound [II] and the compound [III], followed by removing the protecting group when R⁶ and/or R⁷ are a protecting group for amino group.

In the present specification, the lower alkyl group and the lower alkoxy group mean ones having 1 to 6 carbon atoms, preferably 1 to 4 carbon atoms.

The present invention is illustrated in more detail by the following Examples and Reference Examples, but should not be construed to be limited thereto.

EXAMPLE 1

Methyl 5-diphenylacetyl-4,5,6,7-tetrahydroimidazo[4,5-c]pyridine-4-carboxylate (1.60 g) is dissolved in dimethylformamide (20 ml), and thereto is added sodium hydride (60 % oil-dispersion, 176 mg) under ice-cooling. The mixture is stirred at 0° C. for 20 minutes, and thereto is added [2'-(1-trityl-1H-tetrazol-5-yl)biphenyl-4-yl]methyl bromide (2.40 g), and the mixture is stirred under ice-cooling for one hour, and further at room temperature for one hour. The reaction solution is concentrated under reduced pressure, and to the residue are added chloroform and water. The organic layer is dried, and evaporated to remove the solvent. The resulting residue is purified by silica gel column chromatography (solvent; chloroform/methanol=100:1) to give methyl 5-diphenylacetyl-3-[2'-(1-trityl-1H-tetrazol-5-yl)biphenyl-4-yl]methyl-4,5,6,7tetrahydroimidazo[4,5-c]pyridine-4-carboxylate (430 mg) as a colorless foam.

FAB-MS (m/z): 852 (M+H), 792, 610, 567, 244
NMR (CDCl₃)δ: 3.56 (3H, s), 5.12 (2H, ABq)

Subsequently, there is obtained methyl 5-diphenylacetyl-1-[2'-(1-trityl-1H-tetrazol-5-yl)biphenyl-4-yl]methyl-4,5,6,7-tetrahydroimidazo[4,5-c]pyridine-4-carboxylate (1.17 g) as a colorless foam.

FAB-MS (m/z): 852 (M+H), 792, 610, 567, 244
NMR (CDCl₃)δ: 3.79 (3H, s), 4.81 (2H, s)

EXAMPLE 2

To a mixture of methyl 5-diphenylacetyl-3-[2'-(1-trityl-1H-tetrazol-5-yl)biphenyl-4-yl]methyl-4,5,6,7-tetrahydroimidazo[4,5-c]pyridine-4-carboxylate (400 mg) and chloroform (1 ml) is added 18% hydrochloric acid-methanol (5 ml), and the mixture is stirred at room temperature for 30 minutes. After the reaction is completed, the mixture is evaporated to remove the solvent, and the resulting residue is dissolved in methanol (5 ml), and the mixture is adjusted to pH 10-12 with 1N aqueous sodium hydroxide solution, and further stirred at room temperature for 3 hours. The resulting triphenylmethane is removed by extraction with ether, and the aqueous layer is evaporated under reduced pressure. The resulting residue is dissolved in a small amount of water, and purified by column chromatography of non-ionic adsorbing resin (tradename; HP-20, manufactured by Mitsubishi Kasei Corporation, Japan) and lyophilized to give the following compounds.

5-Diphenylacetyl-3-[2'-(1H-tetrazol-5-yl)biphenyl-4-yl]methyl-4,5,6,7-tetrahydroimidazo[4,5-c]pyridine-4-carboxylic acid disodium salt (170 mg)

IR (Nujol; cm⁻¹): 1630

EXAMPLE 3

A mixture of 2-n-butyl-4-(2-aminoethyl)-1-[2'-(1-[2'-(1H-tetrazol-5-yl)biphenyl-4-yl]methylimidazole hydrochloride (8.09 g), glyoxylic acid hydrate (1.73 g), 1N aqueous sodium hydroxide solution (53 ml) and dioxane (50 ml) is stirred at 50° C. for two days. The reaction solution is acidified with hydrochloric acid, and evaporated under reduced pressure. The residue is dissolved in methanol (100 ml), and the mixture is cooled to −30° C., and thereto is added dropwise thionyl chloride (12.4 g). After addition, the mixture is stirred at 60° C. for two days. The mixture is evaporated under reduced pressure to remove the solvent. The mixture is neutralized with aqueous sodium hydrogen carbonate solution, and extracted with chloroform. The extract is dried, and evaporated under reduced pressure, and the resulting oily product is purified by silica gel column chromatography (solvent; chloroform/methanol=15:1) to give methyl 2-n-butyl-3-[2'-(1H-tetrazol-5-yl)biphenyl-4-yl]methyl-4,5,6,7-tetrahydroimidazo[4,5,c]pyridine-4carboxylate (3.74 g) as a powder.

FAB-MS (m/z): 472 (M+H) (base)
NMR (DMSO-d₆)δ: 0.90 (3H, t), 3.72 (3H, S), 5.20 (2H, S)

EXAMPLE 4

To a mixture of the compound obtained in Example 3 (296 mg), triethylamine (317 mg) and chloroform (10 ml) is added dropwise a solution of acetyl chloride (148 mg) in chloroform (1 ml) under ice-cooling. The mixture is stirred at room temperature for two hours, and the reaction solution is washed, dried and evaporated to remove the solvent. The resulting residue is purified by silica gel column chromatography (solvent; chloroform/methanol=30:1) to give methyl 5-acetyl-2-n-butyl-3-[2'-(1H-tetrazol-5-yl)biphenyl-4-yl]methyl-4,5,6,7-tetrahydroimidazo[4,5-c]pyridine-4-carboxylate (158 mg).

FAB-MS (m/z): 514 (M+H), 119 (base)
NMR (CDCl₃)δ: 0.94 (3H, t), 2.16 (3H, s), 3.78 (3H, s)

EXAMPLE 5

A mixture of the compound obtained in Example 3 (361 mg), methylene chloride (10 ml), triethylamine (85 mg), benzoic acid (103 mg), N-hydroxybenzotriazole (114 mg) and 1-ethyl-3-(3-dimethylaminopropyl)carbodiimide hydrochloride (162 mg) is stirred at room temperature overnight. The reaction solution is washed, dried and evaporated to remove the solvent. The resulting oily residue is purified by silica gel column chromatography (solvent; chloroform/methanol=20:1) to give methyl 2-butyl-5-benzoyl-3-[2'-(1H-tetrazol-5-yl)biphenyl-4-yl]methyl-4,5,6,7-tetrahydroimidazo[4,5-c]pyridine-4-carboxylate (297 mg).

FAB-MS (m/z): 576 (M+H), 105 (base)
NMR (CDCl₃)δ: 0.97 (3H, t), 3.79 (3H, s)

EXAMPLE 6

The compound obtained in Example 3 (483 mg) and thiophen-2-carboxylic acid (158 mg) are treated in the same manner as in Example 5 to give methyl 2-n-butyl-5-(2-thienyl)carbonyl-3-[2'-(1H-tetrazol-5-yl)biphenyl-4-yl]methyl-4,5,6,7-tetrahydroimidazo[4,5-c]pyridine-4-carboxylate (306 mg).
FAB-MS (m/z): 582 (M+H), 111 (base)
NMR (CDCl$_3$)δ: 0.95 (3H, t), 3.73 (3H, s)

EXAMPLE 7

A mixture of the compound obtained in Example 3 (2.98 g), 1N aqueous sodium hydroxide solution (14 ml) and methanol (30 ml) is stirred at room temperature overnight, and evaporated to remove the solvent.

The residue is recrystallized from aqueous methanol and collected to give 2-n-butyl-3-[2'-(1H-tetrazol-5-yl)-biphenyl-4-yl]methyl-4,5,6,7-tetrahydroimidazo[4,5-c]pyridine-4-carboxylic acid (2.11 g).
m.p. 216°–217° C. (decomposed).
NMR (DMSO-d$_6$)δ: 0.97 (3H, t), 4.37 (1H, s), 5.17 (1H, d), 6.01 (1H, d).

EXAMPLE 8

A mixture of the compound obtained in Example 4 (142 mg), 1N aqueous sodium hydroxide solution (0.60 ml) and methanol (5 ml) is stirred at room temperature overnight, and evaporated under reduced pressure to remove the solvent. The resulting residue is purified by column chromatography of nonionic adsorbing resin (tradename; NP-20, manufactured by Mitsubishi Kasei Corporation, Japan), and lyophilized to give 2-n-butyl-5-acetyl-3-[2'-(1H-tetrazol-5-yl)biphenyl-4-yl]methyl-4,5,6,7-tetrahydroimidazo[4,5-c]pyridine-4-carboxylic acid disodium salt (100 mg).
m.p. >265° C.
IR (Nujol; cm$^{-1}$): 2620

EXAMPLES 9–10

The compounds obtained in Examples 5–6 are treated in the same manner as in Example 8 to give the following compounds listed in Table 1.

TABLE 1

(Tet: 1H-Tetrazol-5-yl group)

| Ex. | R$^2$ | IR (Nujol; cm$^{-1}$) | m.p. (°C.) |
|---|---|---|---|
| 9 | —CO—(phenyl) | 1620 | >200 (decomposed) |
| 10 | —CO—(thienyl) | 1620 | >72 (wet) |

EXAMPLE 11

(1) To a mixture of 2-n-propyl-4-(2-aminoethyl)-1-[2'-(1-trityl-1H-tetrazol-5-yl)biphenyl-4-yl]methylimidazole (3.66 g) and methanol (30 ml) is added 9% hydrochloric acid-methanol (50 ml), and the mixture is stirred at room temperature for 40 minutes. The mixture is evaporated under reduced pressure to remove the solvent, and water is added to the residue. The mixture is washed with ethyl acetate, and the aqueous layer is evaporated under reduced pressure and further subjected to azeotrophic distillation with toluene to give crude 2-n-propyl-4-(2-aminoethyl)-1-[2'-tetrazol-5-yl)biphenyl-4-yl]methylimidazole hydrochloride (2.68 g).

(2) The above compound (2.15 g) is treated in the same manner as in Example 3 to give methyl 2-n-propyl-3-[2'-(1H-tetrazol-5-yl)biphenyl-4-yl]methyl-4,5,6,7-tetrahydroimidazo[4,5-c]pyridine-4-carboxylate (0.76 g) as a foam.
FAB-MS (m/z): 458 (M+H), 207 (base)
NMR (DMSO-d$_6$)δ: 0.98 (3H, t), 3.84 (3H, s), 5.06 (2H, ABq)

EXAMPLE 12

2-n-Butyl-4-(2-aminoethyl)-1-(2'-methoxycarbonylbiphenyl-4-yl)methylimidazole hydrochloride (1.80 g) is treated in the same manner as in Example 3 to give crude methyl 2-n-butyl-3-(2'-methoxycarbonylbiphenyl-4-yl)methyl-4,5,6,7-tetrahydroimidazo[4,5-c]pyridine-4-carboxylate (1.70 g).

EXAMPLE 13

To a mixture of the compound obtained in Example 12 (1.70 g) and pyridine (20 ml) is added acetic anhydride (5 ml), and the mixture is stirred overnight. The solvent is distilled off, and to the resulting residue is added chloroform, and the mixture is washed, dried, and evaporated to remove the solvent. The residue is purified by silica gel column chromatography (solvent; chloroform/ethanol=10.1) to give methyl 2-n-butyl-5-acetyl-3-(2'-methoxycarbonylbiphenyl-4-yl)methyl-4,5,6,7-tetrahydroimidazo[4,5-c]pyridine-4-carboxylate (0.47 g) as an oil.
NMR (CDCl$_3$)δ: 0.88 (3H, t), 2.21 (3H, s), 3.46 (3H, s), 3.64 (3H), 5.33 (2H, ABq)

EXAMPLE 14

A mixture of 2-n-butyl-4-(2-aminoethyl)-1-[2'-(1H-tetrazol-5-yl)biphenyl-4-yl]methylimidazole hydrochloride (0.278 g), ethyl glyoxylate (0.179 g) and ethanol (5 ml) is refluxed for three days. To the mixture is added chloroform, and the mixture is washed, dried and evaporated to remove the solvent. The solvent is purified by silica gel column chromatography (solvent; chloroform/methanol=10.1) to give ethyl 2-n-butyl-3-[2'-(1H-tetrazol-5-yl)biphenyl-4-yl]methyl-4,5,6,7-tetrahydroimidazo[4,5-c]pyridine-4-carboxylate (0.136 g) as a foam.
NMR (CDCl$_3$)δ: 0.92 (3H, t), 1.35 (3H, t), 5.08 (2H, ABq).

EXAMPLE 15

To a mixture of 2-n-butyl-4-(2-t-butoxycarbonylaminoethyl)-1-(2'-methoxycarbonylbiphenyl-4-yl)methylimidazole (2.02 g) and chloroform (50 ml) is added trifluoroacetic acid (25 ml), and the mixture is stirred at room temperature for 30 minutes. The mixture is evaporated under reduced pressure to remove the solvent, and to the residue are added tetrahydrofurn (30 ml), water (1 ml) and sodiium hydrogen carbonate (1.13 g), and the mixture is stirred. To the mixture is added chloroform, and the mixture is dried, and evaporated under reduced pressure to remove the solvent. To the residue are added ethyl glyoxylate hydrate (0.570 g) and ethanol (40 ml), and the mixture is refluxed for 15 minutes. The solvent is distilled off under reduced pressure, and the resulting residue is purified by silica gel column chromatography (solvent; chloroform/ethanol=20:1) to give ethyl 2-n-butyl-3-(2-'-methoxycarbonylbiphenyl-4-yl)methyl-4,5,6,7-tetrahydroimidazo[4,5-c]pyridine-4-carboxylate (0.551 g) as a foam.

NMR (CDCl$_3$)δ: 0.89 (3H, t), 1.23 (3H, t), 3.65 (3H, s), 5.24 (2H, ABq)

EXAMPLES 16–31

The compounds obtained in Examples 3, 11 and 15 are treated in the same manner as in Example 4 or 5 to give the following compounds listed in Tables 2 and 3.

TABLE 2

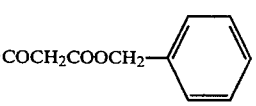

| Ex. | R$^2$ | R$^8$ | R$^9$ | NMR(CDCl$_3$) | FAB-MS (m/z) |
|---|---|---|---|---|---|
| 16 | —COCH$_3$ | CH$_3$ | Tet | 1.04(3H, t) 2.17(3H, s) 3.75(3H, s) | 500 (M+1) 207 (base) |
| 17 | —COCH$_2$COOCH$_2$CH$_3$ | CH$_3$ | Tet | 1.03(3H, t) 1.18(3H, t) 3.73(3H, s) | 572 (M+1) 207 (base) |

Tet: 1H-Tetrazol-5-yl group

TABLE 3

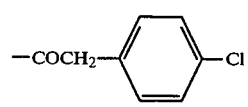

| Ex. | R$^2$ | R$^8$ | R$^9$ | NMR(CDCl$_3$) | FAB-MS (m/z) |
|---|---|---|---|---|---|
| 18 | —COCH$_2$COOCH$_2$—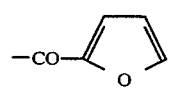 | CH$_3$ | Tet | 0.96(3H, t) 3.59(2H, s) 3.69(3H, s) | 648 (M+1) 154 (base) |
| 19 | —COCH$_2$—〈 〉—Cl | CH$_3$ | Tet | 0.97(3H, t) 3.75(3H, s) 3.78(2H, s) | 624 (M+1) 207 (base) |
| 20 | —CO—〈furan〉 | CH$_3$ | Tet | 0.95(3H, t) 3.75(3H, s) 6.46–6.48 (1H, m) | 566 (M+1) 119 (base) |
| 21 | —CO—〈pyridine〉 | CH$_3$ | Tet | 0.96(3H, t) 3.77(3H, s) 8.58–8.62 (1H, m) | 577 (M+1) 207 (base) |
| 22 | —COCH$_2$CH$_3$ | CH$_3$ | Tet | 0.96(3H, t) | 528 (M+1) |

TABLE 3-continued

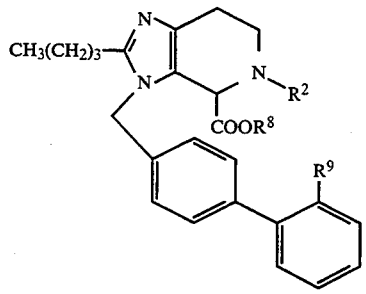

| Ex. | R² | R⁸ | R⁹ | NMR(CDCl₃) | FAB-MS (m/z) |
|---|---|---|---|---|---|
| 23 | —COCH₂CH₂COOCH₃ | CH₃ | Tet | 1.08(3H, t)<br>3.75(3H, s)<br>0.96(3H, t)<br>3.46(3H, s)<br>3.72(3H, s) | 207 (base)<br><br>586 (M+1)<br>207 (base) |
| 24 | —CO—(pyridinyl) | CH₃ | Tet | 0.85–1.01<br>(3H, m)<br>3.80(3H, s)<br>8.66–8.71<br>(1H, m) | 577 (M+1)<br>207 (base) |
| 25 | —COCH(CH₃)₂ | CH₃ | Tet | 0.96(3H, t)<br>1.08(3H, d)<br>1.11(3H, d) | 542 (M+1)<br>207 (base) |
| 26 | —SO₂CH₃ | CH₃ | Tet | 0.96(3H, t)<br>3.00(3H, s)<br>3.77(3H, s) | 550 (M+1)<br>154 (base) |
| 27 | —COOCH₂CH₃ | CH₃ | Tet | 0.94(3H, t)<br>1.23(3H, t)<br>3.69(3H, s) | 544 (M+1)<br>207 (base) |
| 28 | —COCH₂SCH₃ | CH₃ | Tet | 0.96(3H, t)<br>2.11(3H, s)<br>3.75(3H, s) | 560 (M+1)<br>154 (base) |
| 29 | —COCH₂COOCH₂CH₃ | CH₂CH₃ | COOCH₃ | 0.84–0.96<br>(3H, m)<br>3.57(2H, s) | 590 (M+1)<br>225 (base) |
| 30 | —COCH₂COOCH₂CH₃ | CH₃ | Tet | 0.95(3H, t)<br>1.18(3H, t)<br>3.50(2H, s)<br>5.28(2H, ABq)<br>5.40(1H, s) | 586(M+1)<br>207 (base) |
| 31 | —COCH₂CN | CH₃ | Tet | 0.94(3H, t)<br>3.67(3H, s)<br>3.75(3H, s)<br>5.29(2H, s) | 539(M+1) |

Tet: 1H-Tetrazol-5-yl group

EXAMPLE 32

To a mixture of the compound obtained in Example 3 (0.50 g) and methanol (10 ml) is added diketene (0.20 g), and the mixture is stirred at room temperature for two hours. The mixture is evaporated under reduced pressure to remove the solvent, and to the residue is added chloroform. The mixture is washed, dried and evaporated under reduced pressure. The resulting residue is purified by silica gel column chromatography (solvent; chloroform/ethyl acetate/methanol=10:10:1) to give methyl 2-n-butyl-5-acetoacetyl-3-[2'-(1H-tetrazol-5-yl)biphenyl-4-yl]methyl-4,5,6,7-tetrahydroimidazo[4,5-c]pyridine-4-carboxylate (0.29 g) as a foam.

FAB-MS (m/z): 556 (M+1), 207 (base)
NMR (CDCl₃)δ: 0.96 (3H, t), 2.22 (3H, s), 3.74 (3H, s)

EXAMPLE 33

To a mixture of the compound obtained in Example 16 (0.131 g) and methanol (2ml) is added 0.5M aqueous sodium hydrogen carbonate solution (0.53 ml). Five minutes thereafter, the mixture is evaporated under reduced pressure to remove the solvent, and the residue is purified by column chromatography of nonionic adsorbing resin (tradename; NP-20, manufactured by Mitsubishi Kasei Corporation, Japan), and lyophilized to give methyl 2-n-propyl-5-acetyl-3-[2'-(1H-tetrazol-5-yl)biphenyl-4-yl]methyl-4,5,6,7-tetrahydroimidazo[ 4,5-c]pyridine-4-carboxylate sodium salt (0.089 g) as a powder.

m.p. >196² C. (decomposed)
NMR (DMSO-d₆)δ: 0.83–0.92 (3H, m), 1.92 and 2.12 (3H, s), 3.27 and 3.32 (3H, s).

EXAMPLES 34–37

The compounds obtained in Examples 4, 20, 21 and 24 are treated in the same manner as in Example 33 to give the following compounds listed in Table 4.

TABLE 4

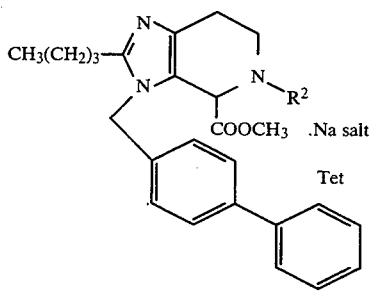

(Tet: 1H-Tetrazol-5-yl group)

| Ex. | R² | NMR(D₂O) |
|---|---|---|
| 34 | —CO—furan | 0.73(3H, t)<br>3.10–3.90(4H, b) |
| 35 | —CO—(2-pyridyl) | 0.82(3H, t)<br>3.25 and 3.56(3H, s) |

TABLE 4-continued

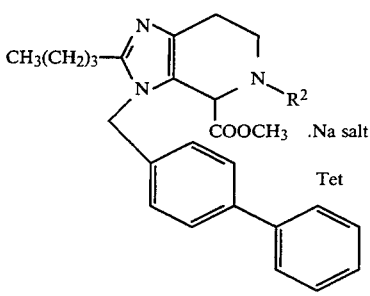

(Tet: 1H-Tetrazol-5-yl group)

| Ex. | R² | NMR(D₂O) |
|---|---|---|
| 36 | —CO—(3-pyridyl) | 0.69–0.81(3H, m)<br>3.23 and 3.62(3H, s) |
| 37 | —COCH₃ | 0.71–0.80(3H, m)<br>3.21 and 3.47(3H, s) |

EXAMPLES 38–46

The compounds obtained in Examples 13, 16, 20–15 and 27 are treated in the same manner as in Example 8 to give the following compounds listed in Table 5.

TABLE 5

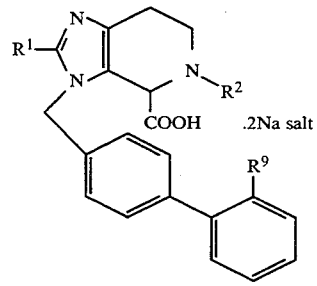

| Ex. | R¹ | R² | R⁹ | IR (Nujol; cm⁻¹) |
|---|---|---|---|---|
| 38 | —(CH₂)₂CH₃ | —COCH₃ | Tet | 1610 |
| 39 | —(CH₂)₃CH₃ | —CO—furan | Tet | 1620 |
| 40 | —(CH₂)₃CH₃ | —CO—(2-pyridyl) | Tet | 1620 |
| 41 | —(CH₂)₃CH₃ | —COCH₂CH₃ | Tet | 1620 |
| 42* | —(CH₂)₃CH₃ | —COCH₂CH₂COOH | Tet | 1620–1560 |
| 43 | —(CH₂)₃CH₃ | —CO—(3-pyridyl) | Tet | 1620 |
| 44 | —(CH₂)₃CH₃ | —COCH(CH₃)₂ | Tet | 1620 |
| 45 | —(CH₂)₃CH₃ | —COOCH₂CH₃ | Tet | 1680, 1610 |
| 46 | —(CH₂)₃CH₃ | —COCH₃ | COOH | 1630–1560 |

*The compound of Example 42 is trisodium salt.
Tet: 1H-Tetrazol-5-yl group

EXAMPLE 47

(1) To a mixture of methyl 2-n-butyl-5-ethoxycarbonylacetyl-3-[2'-(1H-tetrazol-5-yl)biphenyl-4-yl]methyl-4,5,6,7-tetrahydroimidazo[4,5-c]pyridine-4-carboxylate (2.0 g), triethylamine (0.69 g) and chloroform (20 ml) is added trityl chloride (1.43 g), and the mixture is stirred at room temperature for 30 minutes. The reaction solution is washed, dried, and evaporated under reduced pressure. The resulting residue is purified by silica gel column chromatography (solvent; ethyl acetate/n-hexane) to give methyl 2-n-butyl-5-ethoxycarbonylacetyl-3-[2'-(1-trityl-1H-tetrazol-5-yl)biphenyl-4-yl]methyl-4,5,6,7-tetrahydroimidazo[4,5-c]pyridine-4-carboxylate (1.29 g) as needles. m.p. 124°–126° C. (decomposed)

(2) The above product is optically resolved by HPLC column chromatography for separation of optically active isomers (tradename; Chiralcel OD, manufactured by Daicel Chemical Industries, Ltd., Japan) (solvent; n-hexane/ethanol= 7.3) to give the (+)-isomer and the (−)-isomer separately.

The (+)-isomer:
$[\alpha]_D$: +25.2° (c=0.5, chloroform, 25° C.)
The (+)-isomer:
$[\alpha]_D$: −22.8° (c=0.5, chloroform, 25° C.)

EXAMPLE 48

To a mixture of methyl (+)-2-n-butyl-5-ethoxycarbonaylacetyl-3-[2'-(1-trityl-1H-tetrazol-5-yl)biphenyl-4-yl]methyl-4,5,6,7-tetrahydroimidazo[4,5-c]pyridine-4-carboxylate (395 mg) and tetrahydrofuran (4ml) is added 90% formic acid (8ml) under ice-cooling, and the mixture is stirred at room temperature for 30 minutes, and evaporated under reduced pressure to remove the solvent. The resulting residue is purified by silica gel column chromatography (solvent; chloroform/methanol) to give methyl (+)-2-n-butyl-5-ethoxycarbonylacetyl-3-[2'-(1H-tetrazol-5-yl)biphenyl-4-yl]methyl-4,5,6,7-tetrahydroimidazo[4,5-c]pyridine-4-carboxylate (270 mg) as a foam.

$[\alpha]_D$: +70.4° (c=0.5, chloroform, 20° C.)

EXAMPLE 49

Methyl (−)-2-n-butyl-5-ethoxycarbonylacetyl-3-[2'-(1-trityl-1H-tetrazol-5-yl)biphenyl-4-yl]methyl-4,5,6,7-tetrahydroimiadzo]4,5-c]pyridine-4-carboxylate is treated in the same manner as in Example 48 to give methyl (−)-2-n-butyl-5-ethoxycarbonylacetyl-3-[2'-(1H-tetrazol-5yl)biphenyl-4 -yl]methyl-4,5,6,7-tetrahydroimidazo[4,5-c]pyridine-4-carboxylate as a foam.

$[\alpha]_D$: −70.8° (c=0.5, chloroform, 20° C.

EXAMPLE 50

2-n-Propyl-5-(2-aminoethyl)-3-[2'(1-trityl-1H-tetrazol-5-yl)biphenyl-4-yl]methylimidazole (1.01 g) is dissolved in tetrahydrofuran (10 ml), and thereto is added ethyl glyoxylate hydrate (195 mg), and the mixture is stirred at room temperature overnight. The mixture is heated at 50° C. for 30 minutes, and after cooling, 7% hydrochloric acid-methanol solution (3ml) and chloroform (10 ml) are added to the mixture, which is refluxed for 20 minutes. The mixture is evaporated under reduced pressure to remove the solvent, and the resulting residue is dissolved in chloroform (30 ml). To the mixture are added acetic anhydride (290 mg) and a solution of sodium hydrogen carbonate (1.2 g) ini water (20 ml), and the mixture is stirred at room temperature overnight. The mixture is acidified with citric acid, and extracted with chloroform. The extract is washed with water, dried, and evaporated. To the residue are added fumaric acid (100 mg) and ethanol (35 ml), and the mixture is refluxed for 5 hours. Then, the reaction mixture is evaporated under reduced pressure, and the residue is recrystallized from methanol/ether to give ethyl 2-n-propyl-5-acetyl-3-[2'-(1H-tetrazol-5-yl)biphenyl-4-yl]methyl-4,5,6,7-tetrahydroimidazo[4,5-c]pyridine-4-carboxylate ½ fumarate (728 mg).

m.p. 184°–185° C.
Yield: 80%

EXAMPLE 51

To a mixture of 2-n-propyl-4-(2-aminoethyl)-1-[2'-(1-trityl-1H-tetrazol-5-yl)biphenyl-4-yl)methylimidazole (21.95 g) and tetrahydrofuran (200 ml) is added a solution of ethyl glyoxylate hydrate (4.25 g) in tetrahydrofuran (20 ml) at 5° C. The mixture is stirred overnight at room temperature and refluxed for 30 minutes. To a mixture is added a 8% hydrogen chloride ethanol solution (100 ml) at room temperature. The reaction mixture is stirred for 30 minutes, then evaporated. The residue is dissolved in chloroform and washed successively with a saturated sodium hydrogen carbonate solution and brine. The organic layer is dried and evaporated. The oxalate is recrystallized from ethanol to give ethyl 2-n-propyl-3-[2'-(1H-tetrazol-5-yl)biphenyl-4-yl]methyl-4,5,6,7-tetrahydroimidazo[4,5-c]pyridine-4-carboxylate oxalate (10.84 g).

m.p. 140°–142° C.
NMR (DMSO-$d_6$)δ: 0.84 (3H, t), 4.95 (1H, s), 5.29 (2H, brs)
Free carboxylic acid
NMR (CDCl$_3$)δ: 1.00 (3H, t), 3.98 (1H, s), 5.09 (2H, q)

EXAMPLES 52–59

The compound obtained in Example 11 and the corresponding starting compounds are treated in the same manner as in Example 4 or 5 to give the following compounds listed in Tables 6 and 7.

TABLE 6

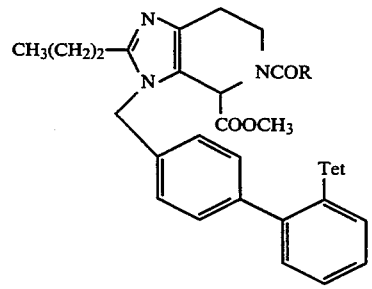

(Tet: 1H-Tetrazol-5-yl group)

| Ex. | R | NMR | FAB-MS (m/z) |
|---|---|---|---|
| 52 | (furan) | 1.01(3H, t) 3.71(3H, s) | 552 (M+ +H) 95 (base) |
| 53 | —CH(CH$_3$)$_2$ | 1.00–1.13(9H) 3.70(3H, s) | 528 (M+ +H) 149 (base) |

TABLE 7

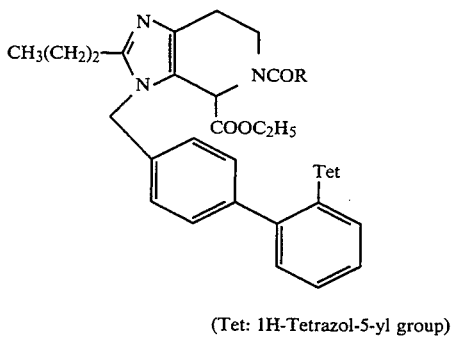

(Tet: 1H-Tetrazol-5-yl group)

| Ex. | R | NMR | FAB-MS (m/z) |
|---|---|---|---|
| 54 | —$CH_2CH_3$ | 1.03(3H, t)<br>5.29(2H, s)<br>5.42(1H, s) | 528 ($M^+$+H)<br>207 (base) |
| 55 | —$(CH_2)_2COOC_2H_5$ | 1.04(3H, t)<br>5.29(2H, ABq)<br>5.32(1H, s) | 600 ($M^+$+H)<br>207 (base) |
| 56 | —$OCH_2CH_3$ | 1.00(3H, t)<br>4.95(1H, s)<br>5.29(2H, s) | 544 ($M^+$+H) (base)<br>207 |
| 57 | —$N(CH_3)_2$ | 1.01(3H, t)<br>5.28(2H, ABq)<br>4.77(1H, s) | 543 ($M^+$+H)<br>72 (base) |
| 58 | —$CH_2CN$ | 0.99(3H, t)<br>1.26(3H, t)<br>1.84(2H, dt)<br>5.95(1H, s) | 539 ($M^+$+H)<br>207 (base) |
| 59 | —$CH_2NHCOCH_3$ | 1.00, 1.03<br>(3H, each t)<br>1.32(3H, t)<br>1.94, 1.97<br>(3H, each s) | 571 ($M^+$+H)<br>207 (base) |

EXAMPLE 60

Ethyl 2-n-propyl-3-[2'-(1H-tetrazol-5-yl)biphenyl-4-yl]methyl-4,5,6,7-tetrahydroimidazo[4,5-c]pyridine-4-carboxylate (1.00 g) is treated in the same manner as in Example 32 with using ethanol instead of methanol to give ethyl 2-n-propyl-5-acetoacetyl-3-[2'-(1H-tetrazol-5-yl)biphenyl-4-yl]methyl-4,5,6,7-tetrahydroimidazo[4,5-c]-pyridine-4-carboxylate (1.00 g) as a white foam.

NMR (CDCl$_3$)δ: 1.03 (3H, t), 2.22 (3H, s), 3.61 (2H, ABq), 5.30 (2H, ABq), 5.36 (1H, s)

EXAMPLE 61

To a mixture of ethyl 2-n-propyl-5-acetoacetyl-3-[2'-(1H-tetrazol-5-yl)biphenyl-4-yl]methyl-4,5,6,7-tetrahydroimidazo[4,5-c]pyridine-4-carboxylate (200 mg), magnesium chloride (34 mg), pyridine (58 μl) and acetonitrile (2 ml) is added benzoyl chloride (42 μl) under ice-cooling. The reaction mixture is stirred overnight at room temperature, then diluted with chloroform (50 ml). The solution is washed with 10% hydrochloric acid and brine, dried, and evaporated to give a crude product (266 mg) as an oil. The product (260 mg) obtained above is refluxed with 10% hydrochloric acid (1.0 ml) in ethnaol (5.0 ml) for one hour. The reaction mixture is diluted with chloroform (30 ml), washed with brine, dried, and then evaporated. Purification by silica gel column chromatography (solvent; chloroform/ethanol) gives ethyl 2-n-propyl-5-benzoylacetyl-3 -[2'-(1H-tetrazol-5-yl)biphenyl-4-yl]methyl-4,5,6,7-tetrahydroimidazo[4,5-c]pyridine-4-carboxylate (144 mg) as a white foam.

FAB-MS (m/z): 618 (MH+), 207 (base)
NMR (CDCl$_3$)δ: 1.04 (3H, t), 4.00–4.28 (5H, m), 5.30 (2H, s), 5.40 (1H, s)

EXAMPLE 62

To a mixture of 2-n-propyl-4-(2-aminoethyl)-1-[2'-(t-butoxycarbonyl)biphenyl-4-yl]methylimidazole (10.0 g) and -tetrahydrofuran (100 ml) is added a solution of ethyl glyoxylate hydrate (2.90 g) in tetrahydrofuran at room temperature. The reaction mixture is stirred overnight, refluxed for 30 minutes, and evaporated. The residue is dissolved in chloroform and the solution is washed with 2% hydrochloric acid solution, a saturated sodium hydrogen carbonate solution and brine. The organic layer is dried and evaporated. The crude product is crystallized with oxalic acid from ethanol-ether to give ethyl 2-n-propyl-3-[2-(t-butoxycarbonyl)biphenyl-4-yl]methyl-4,5,6,7-tetrahydroimidazo[4,5-c]pyridine-4-carboxylate oxalate (8.45 g).

m.p. 166°–168° C.
NMR (DMSO-d$_6$)δ: 0.87 (3H, t), 1.25 (9H, s), 5.10 (1H, s), 5.40 (2H, s)

EXAMPLE 63

The compound obtained in Example 62 (1.00 g) is suspended in chloroform. The suspension is washed with a saturated sodium hydrogen carbonate solution and brine, dried over magnesium sulfate and evaporated. To a mixture of the crude substrate (0.75 g), ethoxycarbonylacetic acid (0.33 g) and methylene chloride (10 ml) is added 1-ethyl-3-(3-dimethylaminopropyl)carbodiimide hydrochloride (0.48 g) at room temperature. The reaction mixture is stirred for one hour, and washed with 10% citric acid solution, a saturated sodium hydrogen carbonate solution and brine. The organic layer is dried and evaporated. The crude product is purified by silica gel column chromatography (solvent; chloroform/ethyl acetate) to give ethyl 2-n-propyl-3-[2'-(t-butoxycarbonyl)biphenyl-4-yl]methyl-5-ethoxycarbonylacetyl-4-carboxylate (0.70 g).

FAB-MS (m/z): 618 (MH+), 211 (base)
NMR (CDCl$_3$)δ: 1.12 (3H, t), 1.28 (9H, s), 3.57 (2H, s), 5.37 (2H, ABq)

EXAMPLE 64

To a mixture of the compound obtained in Example 62 (1.00 g), sodium hydrogen carbonate (1.41 g), chloroform (20 ml) and water (10 ml) is added acetic anhydride (516 mg) at room temperature. The mixture is stirred overnight. The organic layer is separated, washed with brine, dried, and evaporated. Silica gel column chromatography (solvent; chloroform/methanol=20:1) gives ethyl 2-n-propyl-5-acetyl-3-[2'-(t-butoxycarbonyl)biphenyl-4-yl]methyl-4,5,6,7 -tetrahydroimidazo[4,5-c]pyridine-4-carboxylate (0.90 g) as a white foam.

FAB-MS (m/z): 546 (MH+), 211 (base)
NMR (CDCl$_3$)δ: 0.94 (3H, t), 1.28 (9H, s), 5.37 (2H, ABq), 6.02 (1H, s)

EXAMPLE 65

The compound obtained in Example 62 (1.0 g) is treated in the same manner as in Example 64 with using propionyl chloride (0.23 g) instead of acetic anhydride to give ethyl 2-n-propyl-5-propionyl-3-[2'-(t-butoxycarbonyl)biphenyl-4-yl]methyl-4,5,6,7-tetrahydroimidazo[4,5-c]-pyridine-4-carboxylate (0.82 g) as a white foam.

FAB-MS (m/z): 560 (MH+), 211 (base)
NMR (CDCl₃)δ: 0.94 (3H, t), 1.12 (3H, t), 1.18 (3H, t), 1.29 (9H, s)

EXAMPLE 66

The compound obtained in Example 62 (1.00 g) is treated in the same manner as in Example 64 with using ethyl chloroformate (0.27 g) instead of acetic anhydride to give ethyl 2-n-propyl-5-ethoxycarbonyl-3-[2'-(t-butoxycarbonyl)biphenyl-4-yl]methyl-4,5,6,7-tetrahydroimidazo[4,5-c]-pyridine-4-carboxylate (0.82 g) as a white foam.

FAB-MS (m/z): 576 (MH+), 211 (base)
NMR (CDCl₃)δ: 0.95, 0.96 (3H, t), 1.12–1.31 (15H, m), 5.22–5.60 (3H, m)

EXAMPLE 67

The mixture of ethyl 2-n-propyl-3-[2'-(t-butoxycarbonyl)biphenyl-4-yl]methyl-5-ethoxycarbonylacetyl-4,5,6,7-tetrahydroimidazo[4,5-c]pyridine-4-carboxylate (657 mg), trifluoroacetic acid (3 ml) and methylene chloride (10 ml) is stirred overnight at room temperature. The reaction mixture is washed with a saturated sodium hydrogen carbonate solution and brine, dried, and evaporated. The crude product is purified by silica gelcolumn chromatography (solvent; chloroform/methanol) to give ethyl 2-n-propyl-3-(2'-carboxybiphenyl-4-yl)methyl-5-ethoxycarbonylacetyl-4,5,6,7-tetrahydroimidazo[4,5-c]pyridine-4-carboxylate (516 mg).

FAB-MS (m/z): 562 (MH+), 211 (base)
NMR (CDCl₃)δ: 0.76 (3H, t), 3.55 (2H, s), 5.34 (2H, ABq)

EXAMPLES 68–70

The compounds obtained in Examples 64 to 66 are treated in the same manner as in Example 67 to give the following compounds listed in Table 8.

TABLE 8

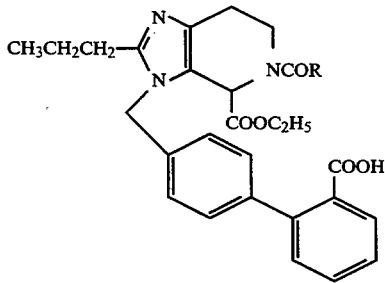

| Ex. | R | NMR(CDCl₃) δ | DI-EI-MS (m/z) |
|---|---|---|---|
| 68 | —CH₃ | 0.79(3H, t) | 489 (M+) |
|   |   | 2.18(3H, s) | 416 (base) |
|   |   | 5.93(1H, s) |   |
| 69 | —C₂H₅ | 0.81(3H, t) | 503 (M+) |
|   |   | 1.15(3H, t) | 430 (base) |
|   |   | 1.18(3H, t) |   |
|   |   | 5.91(1H, s) |   |
| 70 | —OC₂H₅ | 0.68, 0.75(3H, t) | 519 (M+) |
|   |   | 1.13–1.51(8H, m) | 446 (base) |
|   |   | 5.15–5.54(3H, m) |   |

EXAMPLE 71

2-Ethyl-4-(2-aminoethyl)-1-[2'-(1-trityl-1H-tetrazol-5-yl)biphenyl-4-yl]methylimidazole (7.48 g) is dissolved in tetrahydrofuran (60 ml) to which is added ethyl glyoxylate hydrate (1.56 g). The reaction mixture is stirred overnight at room temperature and then refluxed for one hour. The solution is evaporated and the residue is purified by silica gel column chromatography (solvent; chloroform/methanol) to give ethyl 2-ethyl-3-[2'-(1-trityl-1H-tetrazol-5-yl)biphenyl-4-yl]methyl-4,5,6,7-tetrahydroimidazo[4,5-c]pyridine-4-carboxylate (5.54 g) as a foam, characterized as its oxalate.

m.p. 142°–146° C.
NMR (DMSO-d₆)δ: 4.93 (1H, s), 5.23 (2H, s)

EXAMPLE 72

A solution of ethyl 2-ethyl-3-[2'-(1-trityl-1H-tetrazol-5-yl)biphenyl-4-yl]methyl-4,5,6,7-tetrahydroimidazo[4,5-c]pyridine-4-carboxylate (1.94 g), monoethyl malonate (0.74 g), 1-(3-dimethylaminopropyl)-3-ethylcarbodiimide hydrochloride (0.80 g), triethylamine (1.40 g) in dichloromethane (20 ml) is stirred overnight at room temperature. The reaction mixture is washed with water and dried over sodium sulfate, and then evaporated. The residue is dissolved in ethanol (30 ml), fumaric acid (2.00 g) is added, and the solution is refluxed for three hours. The solvent is evaporated and the residue is treated with a saturated sodium hydrogen carbonate solution and then extracted with chloroform. The organic layer is dried and evaporated. Purification by silica gel column chromatography (solvent; chloroform/methanol) gives ethyl 2-ethyl-3-[2'-(1H-tetrazol-5-yl)biphenyl-4-yl]methyl-5-ethoxycarbonylacetyl-4,5,6,7-tetrahydroimidazo[4,5-c]pyridine-4carboxylate (1.07 g) as a foam.

NMR (CDCl₃)δ: 5.29 (2H, s), 5.48 (1H, s), 6.92 (2H, d), 7.10 (2H, d)

EXAMPLE 73

A mixture of ethyl 2-ethyl-3-[2'-(1-trityl-1H-tetrazol-5-yl)biphenyl-4-yl]methyl-4,5,6,7-tetrahydroimidazo[4,5-c]pyridine-4-carboxylate (1.51 g), acetic anhydride (0.44 g), sodium hydrogen carbonate (1.09 g), chloroform (18 ml) and water (18 ml) is stirred overnight at room temperature. The aqueous layer is extracted with chloroform, and the combined organic layer is washed with aqueous citric acid solution and brine, dried, and evaporated. To the residue (1.46 g) is added fumaric acid (1.2 g) and ethanol (20 ml), and the mixture is refluxed for four hours, then evaporated. The residue is treated with a saturated sodium hydrogen carbonate solution and then extracted with chloroform. The organic layer is dried and evaporated. Purification by silica gel column chromatography (solvent; chloroform/methanol) gives ethyl 2-ethyl-5-acetyl-3-[2'-(1H-tetrazol-5-yl)biphenyl-4-yl]methyl-4,5,6,7-tetrahydroimidazo[4,5-c]pyridine-4-carboxylate (0.76 g) as a white foam.

FAB-MS (m/z): 500 (M+1, base), 207
NMR (CDCl₃)δ: 1.30 (3H, t), 2.16 (3H, s), 5.30 (2H, s), 5.45 (1H, s)

EXAMPLE 74

To a solution of 2-ethyl-4-(2-aminoethyl)-1-[2'-(t-butoxycarbonyl)biphenyl-4-yl]methylimidazole (5.30 g) in tetrahydrofuran (40 ml) is added ethyl glyoxylate hydrate (1.67 g). The reaction mixture is stirred overnight at room temperature and then refluxed for two hours. The solvent is evaporated and the residue is purified by silica gel column chromatography (solvent; chloroform/methanol) to give ethyl 2-ethyl-3-[2'-(t-butoxycarbonyl)biphenyl-4-yl]methyl-4,5,6,7-tetrahydroimidazo[4,5-c]pyridine-4-carboxylate (5.90 g) as a yellow oil.

FAB-MS (m/z):-490 (M+1), 211 (base)

NMR (CDCl$_3$)δ: 1.22 (3H, t), 1.28 (9H, s), 1.31 (3H, t), 4.36 (1H, s)

EXAMPLE 75

A mixture of ethyl 2-ethyl-3-[2'-(t-butoxycarbonyl)-biphenyl-4-yl]methyl-4,5,6,7-tetrahydroimidazo[4,5-c]pyridine-4-carboxylate (2.26 g), acetic anhydride (0.94 g), sodium hydrogen carbonate (2.33 g), chloroform (18 ml) and water (18 ml) is stirred overnight at room temperature. The organic layer is separated, washed with brine, dried, and evaporated. The residue is purified by silica gel column chromatography (solvent; chloroform/methanol) to give ethyl 2-ethyl-5-acetyl-3-[2'-(t-butoxycarbonyl)biphenyl-4-yl]methyl-4,5,6,7-tetrahydroimidazo [4,5-c]pyridine-4-carboxylate (2.10 9) as a white foam.

FAB-MS (m/z): 532 (M+1), 211 (base)

NMR (CDCl$_3$)δ: 1.13 (3H, t), 1.28 (9H, s), 2.22 (3H, s), 6.05 (1H, s)

EXAMPLE 76

A solution of ethyl 2-ethyl-3-[2'-(t-butoxycarbonyl)-biphenyl-4-yl]methyl-4,5,6,7-tetrahydroimidazo[4,5-c]pyridine-4-carboxylate (1.72 g), monoethyl malonate (0.94 g), 1-(3-dimethylaminopropyl)-3-ethylcarbodiimide hydrochloride (1.02 g), triethylamine (1.78 g) in dichloromethane (20 ml) is stirred overnight at room temperature. The reaction mixture is washed with water and dried over sodium sulfate and then evaporated. The residue is purified by silica gel column chromatography (solvent; chloroform/methanol) to give ethyl 2-ethyl-3-[2'-(t-butoxycarbonyl)biphenyl-4-yl]methyl-5-ethoxycarbonylacetyl-4,5,6,7-tetrahydroimidazo[4,5-c]pyridine-4-carboxylate (1.57 g) as an oil.

NMR (CDCl$_3$)δ: 1.12 (3H, t), 1.28 (9H, s), 5.35 (2H, q), 6.00 (1H, s)

EXAMPLE 77

To a solution of the above product (2.05 g) in dichloromethane (20 ml) is added trifluoroacetic acid (6 ml). The reaction mixture is stirred at room temperature overnight, and then evaporated. The residue is dissolved in chloroform and washed with a saturated sodium hydrogen carbonate solution. The organic layer is dried over sodium sulfate and then concentrated to give the crude product which is purified by silica gel column chromatography (solvent; chloroform/methanol) to give ethyl 2-ethyl-3-(2'-carboxybiphenyl-4-yl)methyl-5-ethoxycarbonylacetyl-4,5,6,7-tetrahydroimidazo[4,5-c]pyridine-4-carboxylate (1.17 g) as white foam.

NMR (CDCl$_3$)δ: 0.98 (3H, t), 1.16 (3H, t), 1.27 (3H, t), 5.33 (2H, q), 6.00 (1H, s)

EXAMPLE 78

The compound obtained in Example 75 (2.05 g) is treated in the same manner as in Example 67 to give ethyl 2-ethyl-5-acetyl-3-(2'-carboxybiphenyl-4-yl)methyl-4,5,6,7-tetrahydroimidazo[4,5-c]pyridine-4-carboxylate (1.53 g) as a white foam.

FAB-MS (m/z): 476 (M+1), 211 (base)

NMR (CDCl$_3$)δ: 1.00 (3H, t), 2.20 (3H, s), 6.00 (1H, s), 6.95 (2H, d)

EXAMPLE 79

A mixture of ethyl 2-n-propyl-3-[2'-(t-butoxycarbonyl)biphenyl-4-yl]methyl-4,5,6,7-tetrahydroimidazo[4,5-c]pyridine-4-carboxylate (0.20 g), potassium carbonate (0.082 g), allyl bromide (0.057 g) and tetrahydrofuran (2 ml) is stirred overnight at room temperature. To the mixture is added chloroform, and the mixture is washed, dried and evaporated. The residue is purified by silica gel column chromatography (solvent; chloroform/methanol) to give ethyl 2-n-propyl-5-allyl-3-[2'-(t-butoxycarbonyl)biphenyl-4-yl] methyl-4,5,6,7-tetrahydroimidazo[4,5-c]pyridine-4-carboxylate (0.128 g).

FAB-MS (m/z): 544 (M+1), 211 (base)

NMR (CDCl$_3$)δ: 0.96 (3H, t), 1.19 (3H, t), 1.30 (9H, s), 4.25 (1H, s)

EXAMPLE 80

To a mixture of ethyl 2-n-propyl-3-[2'-(t-butoxycarbonyl)biphenyl-4-yl]methyl-4,5,6,7-tetrahydroimidazo[4,5-c]pyridine-4-carboxylate (0.65 g), potassium carbonate (0.533 g) and dimethylformamide (6 ml) is added benzyl bromide (0.33 g). The mixture is stirred at room temperature for one hour, then diluted with ethyl acetate. The solution is washed with water, dried, and evaporated. The residue is purified by silica gel column chromatography (solvent; chloroform/methanol) to give ethyl 2-n-propyl-5-benzyl-3-[2'-(t-butoxycarbonyl)biphenyl-4-yl]methyl-4,5,6,7-tetrahydroimidazo[4,5-c]pyridine-4-carboxylate (0.49 g).

FAB-MS (m/z) 594 (M+1), 91 (base)

NMR (CDCl$_3$)δ: 0.96 (3H, t), 1.16 (3H, t), 1.28 (9H, s), 4.22 (1H, s)

EXAMPLE 81

The compound obtained in Example 79 is treated in the same manner as in Example 67 to give ethyl 2-n-propyl-5-allyl-3-(2'-carboxybiphenyl-4-yl)methyl-4,5,6,7-tetrahydroimidazo[4,5-c]pyridine-4-carboxylate.

FAB-MS (m/z): 488 (M+1), 43 (base)

NMR (CDCl$_3$)δ: 0.74 (3H, t), 1.18 (3H, t), 4.34 (1H, s)

EXAMPLE 82

The compound obtained in Example 80 is treated in the same manner as in Example 67 to give ethyl 2-n-propyl-5-benzyl-3-(2'-carboxybiphenyl-4-yl)methyl-4,5,6,7-tetrahydroimidazo[4,5-c]pyridine-4-carboxylate.

FAB-MS (m/z): 538 (M+1), 91 (base)

NMR (CDCl$_3$)δ: 0.77 (3H, t), 1.09 (3H, t), 3.63 (1H, d), 3.76 (1H, d), 4.18 (1H, s)

EXAMPLE 83

A mixture of 2-n-propyl-4-(2-aminoethyl)-1-[2'-(1-trityl-1H-tetrazol-5-yl)biphenyl-4-yl]methylimidazole (6.92 g), ethyl glyoxylate hydrate (1.30 g) and tetrahydrofuran (70 ml) is stirred overnight at room temperature. The mixture is evaporated, and the residue is purified by silica gel column chromatography (solvent; chloroform/ethanol) to give ethyl 2-n-propyl-3-[2'-(1-trityl-1H-tetrazol-5-yl)biphenyl-4-yl]methyl-4,5,6,7-tetrahydroimidazo[4,5-c]pyridine-4-carboxylate (5.32 g) as a foam.

FAB-MS (m/z): 714 (M+1), 243 (base)

NMR (CDCl$_3$)δ: 0.90 (3H, t), 1.21 (3H, t), 1.92 (brs), 4.17 (1H, s), 5.10 ( 2H, ABq)

EXAMPLE 84

A mixture of ethyl 2-n-propyl-3-[2'-(1-trityl-1 H-tetrazol-5-yl)biphenyl-4-yl]methyl-4,5,6,7-tetrahydroimidazo[4,5-c]pyridine-4-carboxylate (2.00 g), potassium carbonate (1.16 g), ethyl bromide (0.61 g) and dimethylformamide (10 ml) is stirred overnight at room temperature. The mixture is diluted with ethyl acetate, and the solution is washed with water, dried and evaporated. The residue is purified by silica gel column chromatography (solvent; chloroform/methanol) to give ethyl 5-ethyl-2-n-propyl-3-[2'-(1-trityl-1H-tetrazol-5-yl)biphenyl-4-yl]methyl-4,5,6,7-tetrahydroimidazo[4,5-c]pyridine-4-carboxylate (1.12 g) as a white foam.

FAB-MS (m/z): 742 (M+1), 243 (base)

NMR (CDCl$_3$)δ: 0.88 (3H, t), 0.97 (3H, t), 1.15 (3H, t), 4.15 (1H, s)

EXAMPLE 85

A mixture of ethyl 2-n-propyl-3-[2'-(1-trityl-1H-tetrazol-5-yl)biphenyl-4-yl]methyl-4,5,6,7-tetrahydroimidazo[4,5-c]pyridine-4-carboxylate (2.00 g), potassium carbonate (1.16 g), benzyl bromide (0.72 g) and dimethylformamide (10 ml) is stirred under ice-cooling for two hours. The mixture is diluted with ethyl acetate, and the solution is washed with water, dried and evaporated. The residue is purified by silica gel column chromatography (solvent; n-hexane/ethyl acetate) to give ethyl 5-benzyl-2-n-propyl-3-[2'-(1-trityl-1H-tetrazol-5-yl)biphenyl-4-yl]-methyl-4,5,6,7-tetrahydroimidazo[4,5-c]pyridine-4 -carboxylate (1.50 g) as a white foam.

FAB-MS (m/z): 804 (M+1), 243 (base)

NMR (CDCl$_3$)δ: 0.87 (3H, t), 1.13 (3H, t), 3.64 (1H, d), 3.77 (1H, d), 4.13 (1H, s)

EXAMPLE 86

A mixture of ethyl 5-ethyl-2-n-propyl-3-[2'-(1-trityl-1H-tetrazol-5-yl)biphenyl-4-yl]methyl-4,5,6,7-tetrahydroimidazo[4,5-c]pyridine-4-carboxylate (1.10 g), fumaric acid (1.2 g) and ethanol (20 ml) is refluxed for one hour. The mixture is evaporated, and the residue is dissolved in chloroform, and the mixture is washed with a saturated sodium hydrogen carbonate solution and brine, dried and evaporated. The residue is purified by silica gel column chromatography (solvent; chloroform/methanol) to give ethyl 5-ethyl-2-n-propyl-3-[2'-(1H-tetrazol-5-yl)biphenyl-4-yl]methyl-4,5,6,7-tetrahydroimidazo[4,5-c]pyridine-4-carboxylate (0.65 g) as a white foam.

FAB-MS (m/z): 500 (M+1), 43 (base)

NMR (CDCl$_3$)δ: 0.88 (3H, t), 0.99 (3H, t), 1.05 (3H, t), 4.05 (1H, s)

EXAMPLE 87

The compound obtained in Example 85 is treated in the same manner as in Example 86 to give ethyl 5-benzyl-2-n-propyl-3-[2'-(1H-tetrazol-5-yl)biphenyl-4-yl]methyl-4,5,6,7-tetrahydroimidazo[4,5-c]pyridine-4-carboxylate.

FAB-MS (m/z): 562 (M+1), 91 (base)

NMR (CDCl$_3$)δ: 0.89 (3H, t), 1.03 (3H, t), 3.54 (1H, d), 3.68 (1H, d), 4.02 (1H, s)

EXAMPLES 88–102

The compounds obtained in Examples 52 to 56, 59, 68 to 70, 73, 78, 81, 82, 86 and 87 are treated in the same manner as in Example 8 to give the following compounds listed in Tables 9 to 12.

TABLE 9

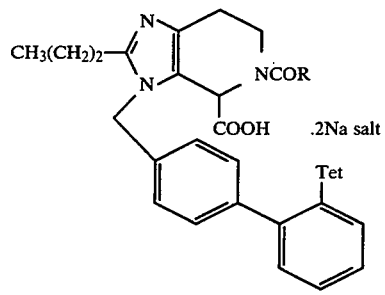

(Tet: 1H-Tetrazol-5-yl group)

| Ex. | R | NMR(D$_2$O) δ | FAB-MS (m/z) |
|---|---|---|---|
| 88 | (furan) | 0.87(3H, t) | 582 (M+1) |
|  |  | 6.23(2H, dd) | 155 (base) |
| 89 | —CH(CH$_3$)$_2$ | 0.89(3H, t) | 558 (M+1) |
|  |  | 0.44, 0.96, 1.04, 1.14 | 154 (base) |
|  |  | (6H, d) |  |
| 90 | —CH$_2$CH$_3$ | 0.70–1.19(6H, m) | 566 (M+Na) |
|  |  | 5.14–5.78(3H, m) | 544 (M+1) |
|  |  |  | 154 (base) |
| 91 | —(CH$_2$)$_2$COONa | 0.76–0.92 (6H, m) | 632 (M+Na) |
|  |  | 5.18–5.78(3H, m) | 610 (M+1) |
|  |  |  | 154 (base) |
| 92 | —OCH$_2$CH$_3$ | 0.82(3H, t) | 582 (M+Na) |
|  |  | 0.94, 1.26(3H, t) | 560 (M+1) |
|  |  |  | 154 (base) |
| 93 | —CH$_2$NHCOCH$_3$ | 0.81, 0.93(3H, each t) | 609 (M+Na) |
|  |  | 4.06, 4.56(1H, each dd) | 587 (M+1) |
|  |  | 4.45, 5.68(1H, each s) | 154 (base) |

TABLE 10

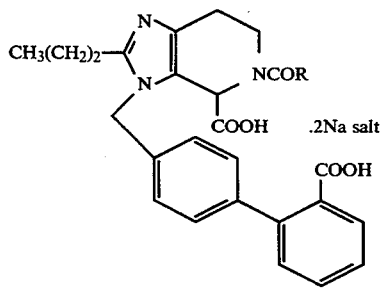

| Ex. | R | m.p. | NMR(D$_2$O) | FAB-MS (m/z) |
|---|---|---|---|---|
| 94 | —CH$_3$ | >300° C. | 0.88, 0.95 | 528 (M+Na) |
|  |  |  | (3H, each t) | 506 (M+1) |
|  |  |  | 1.72, 2.21 | 177 (base) |
|  |  |  | (3H, each s) |  |
| 95 | —CH$_2$CH$_3$ | >300° C. | 0.72, 0.87 | 542 (M+Na) |
|  |  |  | (3H, each t) | 520 (M+1) |
|  |  |  | 0.97, 1.10 |  |
|  |  |  | (3H, each t) |  |
| 96 | —OCH$_2$CH$_3$ | >280° C. | 0.86(3H, t) | 582 (M+Na) |
|  |  |  | 1.27(3H, t) | 560 (M+1) |
|  |  |  |  | 177 (base) |

TABLE 11

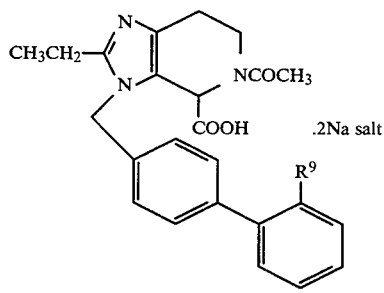

.2Na salt

| Ex. | R⁹ | NMR (D₂O) δ | FAB-MS (m/z) |
|---|---|---|---|
| 97 | Tet | 1.06–1.16(3H, m)<br>1.71, 2.04(3H, each s)<br>5.50, 6.01(1H, each s) | 538 (M+Na)<br>516 (M+1)<br>177 (base) |
| 98 | —COOH | 1.15(3H, t)<br>1.75, 2.03(3H, each s)<br>5.97, 6.31(1H, each s) | 514 (M+Na)<br>492 (M+1)<br>177 (base) |

Tet: 1H-Tetrazol-5-yl group

TABLE 12

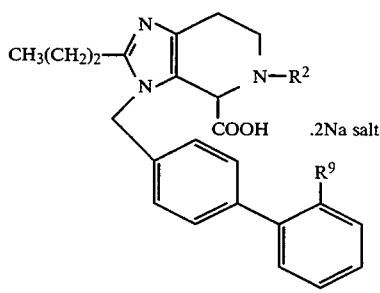

.2Na salt

| Ex. | R² | R⁹ | NMR (D₂O) | FAB-MS (m/z) |
|---|---|---|---|---|
| 99 | —CH₂CH₃ | Tet | 0.82(3H, t)<br>0.99(3H, t)<br>4.01(1H, s) | 538 (M+Na)<br>516 (M+1)<br>177 (base) |
| 100 | —CH₂—C₆H₅ | Tet | 0.88(3H, t)<br>3.84(1H, s)<br>4.94(1H, d) | 600 (M+Na)<br>578 (M+1)<br>177 (base) |
| 101 | —CH₂CH=CH₂ | —COOH | 0.90(3H, t)<br>3.99(1H, s)<br>7.05(2H, d) | 526 (M+Na)<br>504 (M+1)<br>177 (base) |
| 102 | —CH₂—C₆H₅ | —COOH | 0.93(3H, t)<br>3.52(1H, d)<br>3.78(1H, d) | 544 (M+1)<br>177 (base) |

Tet: 1H-Tetrazol-5-yl group

EXAMPLE 103

To a solution of ethyl 2-n-propyl-5-acetyl-3-[2'-(1H-tetrazol-5-yl)biphenyl-4-yl]methyl-4,5,6,7-tetrahydroimidazo[4,5-c]pyridine-4-carboxylate (50.0 g) in methanol (500 ml) is added 4N aqueous sodium hydroxide solution (50 ml) under ice-cooling. The mixture is stirred overnight at room temperature, then evaporated. The residue is recrystallized from ethanol to give 2-n-propyl-5-acetyl-3-[2'-(1H-tetrazol-5-yl)biphenyl-4-yl]methyl-4,5,6,7-tetrahydroimidazo[4,5-c]pyridine-4-carboxylic acid disodium salt (44.3 g).

m.p. >300° C.

FAB-MS (m/z): 552 (M+Na), 530 (M+1), 177 (base)
NMR (D₂O)δ: 0.81–0.93 (3H, m), 1.67, 2.02 (3H, each s), 4.53, 5.44 (1H, each s)

REFERENCE EXAMPLE 1

Methyl 4,5,6,7-tetrahydroimidazo[4,5-c]pyridine-4-carboxylate is treated in the same manner as Example 5 to give methyl 5-diphenylacetyl-4,5,6,7-tetrahydroimidazo[4,5-c]pyridine-4-carboxylate as a pale yellow foam.

NMR (CDCl₃)δ: 3.68 (3H, s), 6.07 (1H, s)

REFERENCE EXAMPLE 2

(1) 1-t-Butoxycarbonyl-4-[2-(t-butoxycarbonylamino)ethyl]imidazole (78.1 g) is dissolved in acetonitrile (500 ml), and thereto is added methoxymethyl chloride (22.2 g). The mixture is stirred at room temperature overnight, and poured into aqueous 10% sodium carbonate solution, and extracted with ethyl acetate. The extract is washed, dried and evaporated to give 5-[2-(t-butoxycarbonylamino)ethyl]-1methoxymethylimidazole (54.4 g) as an oil.

NMR (CDCl₃)δ: 1.43 (9H, s), 3.27 (3H, s), 5.20 (2H, s)

(2) The above compound (55 g) is dissolved in tetrahydrofuran (1.5 liter), and the mixture is cooled to −40° C. To the mixture is added dropwise 1.6M n-butyl lithium/n-hexane solution (150 ml), and the mixture is stirred for 30 minutes. To the mixture is added hexamethylphosphamide (150 ml), and thereto is further added n-butyl lithium (137 ml), and n-butyl iodide (37.5 g) is added dropwise to the mixture while the temperature thereof is kept at −30° C. The mixture is stirred for 10 minutes, and the reaction is quenched with aqueous ammonium chloride solution. Ethyl acetate is added to the reaction mixture, and the organic layer is collected, washed, dried and evaporated to remove the solvent. The resulting oily residue is purified by silica gel column chromatography (solvent; chloroform/ethyl acetate/methanol=32:8:1) to give 5-[2-(t-butoxycarbonylamino)ethyl]-2-n-butyl-1-methoxymethylimidazole (44.8 g) as an oil.

NMR (CDCl$_3$)δ: 0.94 (3H, t), 1.44 (9H, s), 3.27 (3H, s), 5.09 (2H, s)

(3) A mixture of the above compound (80.7 g), ethyl chorocarbonate (84.5 g) and chloroform (1.3 liter) is refluxed for 2.5 hours, and evaporated to remove the solvent. Ethanol (300 ml) and 10% aqueous sodium hydroxide solution (200 ml) are added to the residue, and the mixture is stirred under ice-cooling for 20 minutes. The solvent is distilled off, and chloroform and water are added to the residue. The chloroform layer is dried and evaporated. The resulting residue is recrystallized from isopropyl ether to give 4-[2-(t-butoxycarbonylamino)ethyl]-2-n-butylimidazole (50.3 g).

m.p. 118°–120° C.

(4) The above compound is treated in the same manner as in Example 1 to give 4-[2-(t-butoxycarbonylamino)ethyl]-2-n-butyl-1-[2'-(1-trityl-1H-tetrazol-5-yl)biphenyl-4-yl]methylimidazole.

NMR (CDCl$_3$)δ: 0.89 (3H, t), 1.43 (9H, s), 4.85 (2H, s)

(5) A mixture of the above compound (15.2 g), 10% hydrochloric acid (40 ml) and methanol (60 ml) is refluxed for one hour. After the reaction is completed, the mixture is evaporated to remove the methanol, and the aqueous layer is washed and concentrated to dryness under reduced pressure. The resulting residue is subjected to azeotropic distillation with dry toluene to give crude 2-n-butyl-4-(2-aminoethyl)-1-[2'-(1H-tetrazol-5-yl)biphenyl-4-yl]methylimidazole hydrochloride (9.7 g) as a caramel.

FAB-MS (m/z): 402 (M+H) (base)

NMR (DMSO-d$_6$)δ: 0.84 (3H, t), 1.43 (9H, s), 5.40 (2H, s)

REFERENCE EXAMPLE 3

(1) 2-Propyl-4-hydroxymethylimidazole (2.61 g) is added to thionyl chloride (4.5 ml), and the mixture is heated at 50° C. for two hours. The solvent is distilled off, and the residue is dissolved in dimethylformamide (20 ml), and the mixture is added dropwise to a solution of sodium cyanide (5.47 g) in dimethylformamide (120 ml). The mixture is stirred at room temperature overnight, and evaporated to remove the solvent. To the resulting residue is added ethyl acetate, and the mixture is washed, dried and evaporated. The residue is purified by silica gel column chromatography (solvent; ethyl acetate) to give 2-n-propyl-4-cyanomethylimidazole (3.08 g) as an oil.

NMR (CDCl$_3$)δ: 0.95 (3H, t), 3.67 (2H, d)

(2) The above product (3.08 g) is dissolved in acetic acid (30 ml), and thereto is added 10% hydrochloric acid (10 ml). The mixture is subjected to catalytic hydrogenation using platinum oxide as a catalyst. After the reaction is completed, platinum oxide is removed by filtration, and the filtrate is evaporated under reduced pressure to give 2-n-propylhistamine hydrochloride (4.83 g).

(3) A mixture of the above compound (4.83 g), phthalic anhydride (3.04 g), sodium acetate (6.10 g) and acetic acid (50 ml) is refluxed for 19 hours. The mixture is evaporated under reduced pressure, and water is added to the resulting residue. The mixture is neutralized with sodium hydrogen carbonate, and extracted with chloroform. The extract is dried, and evaporated, and the resulting residue is purified by silica gel column chromatography (solvent; chloroform/methanol=20:1) to give 2-n-propyl-4-(2-phthalimidethyl)imidazole (2.72 g).

m.p. 137°–139° C.

NMR (CDCl$_3$)δ: 0.90 (3H, t), 3.95 (2H, t), 7.61–7.86 (4H, m)

REFERENCE EXAMPLE 4

The compound obtained in Reference Example 3 is treated in the same manner as in Example 1 to give 2-n-propyl-4-(2-phthalimidethyl)-1-[2'-(1-trityl-1H-tetrazol-5-yl)biphenyl-4-yl]methylimidazole as foam.

NMR (CDCl$_3$)δ: 0.86 (3H, t), 4.82 (2H, s)

Oxalate m.p. 112° C. (sintered)

REFERENCE EXAMPLE 5

To a mixture of the compound obtained in Reference Example 4 (4.11 g) and ethanol (100 ml) is added 10% hydrazine hydrate (2 ml), and the mixture is stirred at room temperature for 5 hours. After the reaction is completed, chloroform is added to the reaction mixture, and the mixture is washed, dried and evaporated to give crude 2-n-propyl-4-(2-aminoethyl)-1-[2'-(1-trityl-1H-tetrazol-5-yl)biphenyl-4-yl]methylimidazole (3.68 g) as an oil.

REFERENCE EXAMPLE 6

4-[2-(t-Butoxycarbonylamino)ethyl]-2-n-butylimidazole (3.0 g) and methyl 4'-bromomethylbiphenyl-2-carboxylate (3.75 g) are treated in the same manner as in Example 1 to give 2-n-butyl-4-(2-t-butoxycarbonylaminoethyl)-1-[2'-methoxycarbonylbiphenyl-4-yl]methylimidazole (2.65 g) as an oil.

EI-MS (m/z): 491 (M+), 225 (base)

NMR (CDCl$_3$)δ: 0.91 (3H, t), 3.66 (3H, s), 5.02 (2H, s)

REFERENCE EXAMPLE 7

A mixture of the compound obtained in Reference Example 6, 10% hydrochloric acid (40 ml) and methanol (60 ml) is refluxed for one hour. After the reaction is complete, the mixture is evaporated to remove the methanol, and the aqueous layer is washed and concentrated to dryness under reduced pressure. The resulting residue is subjected to azeotropic distillation with dry toluene to give crude 2-n-butyl-4-(2-aminoethyl)-1-(2'-methoxycarbonylbiphenyl-4-yl)methylimidazole hydrochloride.

REFERENCE EXAMPLE 8

(1) n-Butanamidine hydrochloride (5.0 g) and potassium carbonate (11.4 g) are suspended in acetonitrile (100 ml), and the mixture is heated at 80° C. to 90° C. To the mixture is added dropwise a solution of 1-bromo-4-phthalimidbutan-2-one (10.0 g) in acetonitrile (200 ml) with stirring, and the mixture is heated at the same temperature for 1.5 hour. The insoluble materials are removed by filtration, and the filtrate is concentrated. The resulting residue is dissolved in ethyl acetate, washed with water, dried over sodium sulfate, and evaporated. Fumaric acid is added to the residue, and the product is recrystallized from ethanol/ether to give 2-n-propyl-4-(2-phthalimidethyl)imidazole ½ fumarate (9.9 g).

m.p. 185°–187° C.

(2) The above fumarate (13.7 g) is suspended in ethyl acetate/water, and thereto is added sodium hydrogen carbonate (5.8 g) to give 2-n-propyl-4-(2-phthalimidethyl)imidazole (9.24 g). To a solution of the product (9.24 g) and 4-(2'-cyanophenyl)benzyl bromide (9.3 g) in tetrahydrofuran (150 ml) and dimethylformamide (10 ml) is added dropwise a solution of potassium t-butoxide (3.84 g) in tetrahydrofuran (50 ml) at 50° C. The mixture is allowed to warm to 20° C., and stirred for two hours. The reaction is quenched with aqueous ammonium chloride solution, and the mixture is extracted with ethyl acetate, and the ethyl acetate layer is washed with water, and dried over sodiumسulfate, and evaporated to give a colorless oily product (15.3 g). The product is dissolved in ethanol, and thereto is added oxalic acid, and the product is recrystallized from ethanol to give 2-n-propyl-4-(2-phthalimidethyl)-1-(2'-cyanobiphenyl-4-yl)methylimidazole oxalate (13.44 g).

m.p. 162°–166° C.

NMR (DMSO-d$_6$)δ: 0.82 (3H, t), 2.60–3.10 (4H, m), 5.34 (2H, s)

(3) A mixture of 2-n-propyl-4-(2-phthalimidethyl)-1-(2'-cyanobiphenyl-4-yl)methylimidazole (0.5 g) and tributyltin azide (0.70 g) is heated overnight at 110° C. To the reaction mixture is added 8% hydrogen chloride ethanol solution (5 ml), and the solution is stirred for 30 minutes at room temperature, then evaporated. The residue is dissolved in water (30 ml), and the solution is washed with ether. The aqueous layer is neutralized with sodium hydrogen carbonate, and extracted with chloroform. The chloroform solution is dried, and evaporated. To the residue (575 mg) are added triphenylchloromethane (0.38 g), triethylamine (0.20 ml) and chloroform (5.0 ml). The solution is stirred for two hours at room temperature, then washed with a saturated sodium hydrogen carbonate solution and brine, dried over sodium sulfate, and evaporated. To the residue is added oxalic acid (0.10 g), and the mixture is recrystallized from ethanol to give 2-n-propyl-4-(2-phtalimidethyl)-1-[2'-(1-trityl-1H-tetrazol-5-yl)biphenyl-4-yl]methylimidazole oxalate (0.70 g).

m.p. 112° C. (sintered)

REFERENCE EXAMPLE 9

To a solution of 1-(diethoxy)methylimidazole (260 g) in tetrahydrofuran (5 liters) is added dropwise 1.6M solution of n-butyl lithium in hexane (1 liter) at −45° C. Thirty minutes thereafter, n-butyl iodide (294 g) is added dropwise to the mixture at the same temperature. The reaction mixture is stirred overnight at room temperature and then evaporated. To the residue is added ether (2 liters), and the solution is extracted with 10% hydrochloric acid. The aqueous solution is basified with 10 sodium hydroxide solution, then evaporated with chloroform. The organic layer is washed, dried and evaporated. To the crude product (204 g), triethylamine (170 g) and chloroform (2 liters) is added dropwise a solution of dimethylsulfamoyl chloride (200 g) in chloroform (200 ml) under ice-cooling. The mixture is stirred overnight at room temperature, washed with brine, dried, and evaporated. The crude product is purified by distillation to give 2-n-butyl-1-dimethylsulfamoylimidazole (249.4 g).

b.p. 124° C. (1 mmHg)

REFERENCE EXAMPLE 10

1-(Diethoxy)methylimidazole and n-propyl lithium are treated in the same manner as in Reference Example 9 to give 2-n-propyl-1-dimethylsulfamoylimidazole.

b.p. 141°–143° C. (3 mmHg)

REFERENCE EXAMPLE 11

To a stirred solution of 2-ethylimidazole (100 g) and triethylamine (115 g) in chloroform (800 ml) at 0° C. is added a solution of dimethylsulfamoyl chloride (153 g) in chloroform (200 ml). The mixture is stirred overnight at room temperature. Water (1.5 liter) is added to the reaction mixture after which the organic layer is separated and concentrated. The residue is dissolved in ethyl acetate (1 liter) and washed with water, and then dried over sodium sulfate and concentrated. Distillation gives 1-dimethylsulfamoyl-2-ethylimidazole (182 g) as a colorless liquid.

b.p. 139°–142° C. (5 mmHg)

NMR (CDCl$_3$)δ: 1.37 (3H, t), 2.89 (6H, s), 6.94 (1H, d), 7.23 (1H, d)

REFERENCE EXAMPLE 12

To a stirred solution of the above product (53 g) in tetrahydrofuran (1 liter) at −78° C. is added 1.6M solution of n-butyl lithium in hexane (185 ml). The solution is stirred at −78° C. for one hour, and thereto is added a solution of 1-t-butexycarbonylaziridine (52 g) in tetrahydrofuran (300 ml), and further added thereto boron trifluoride etherate (147 g). The reaction mixture is stirred for another two hours at −78° C. after which it is poured into an ice-cooled saturated aqueous solution of potassium carbonate (2 liters). After evaporation of the remaining tetrahydrofuran, the aqueous layer is extracted with ethyl acetate, washed with water and dried over sodium sulfate, and then concentrated. The residue is purified by silica gel column chromatography (solvent; chloroform/methanol) to give 1-dimethylsulfamoyl-2-ethyl-5-[2-(t-butoxycarbonylamino)ethylimidazole (67 g) as a yellow oil.

NMR (CDCl$_3$)δ: 1.35 (3H, t), 1.43 (9H, s), 2.87 (6H, s), 6.72 (1H, s)

REFERENCE EXAMPLE 13

A solution of the above product (67 g) in 10% hydrochloric acid (600 ml) is refluxed for two hours. The solvent is distilled off under reduced pressure and the resulting oily black residue is dissolved in acetic acid (300 ml). After addition of sodium acetate (62 g) and phthalic anhydride (34 g), the reaction mixture is refluxed overnight. The reaction mixture is concentrated under reduced pressure and the residue is triturated in acetone (300 ml) to give the crude 2-ethyl-4-(2-phthalimidethyl)imidazole (26 g) as a white powder. This product is used in the next reaction without further purification.

REFERENCE EXAMPLE 14

To a solution of the above product (6.56 g) and 2'-(1-trityl-1H-tetrazol-5-yl)biphenyl-4-ylmethyl bromide (16.3 g) in tetrahydrofuran (100 ml) dimethylformamide (50 ml) at −60° C. is added potassium t-butoxide (3.01 g). The reaction mixture is allowed to slowly warm to room temperature in 5 hours and then poured into brine (2 liters), extracted with ethyl acetate, washed with brine and dried over sodium sulfate. After concentration, the residue is purified by silica gel column chromatography (solvent; hexane/ethyl acetate) to give 2-ethyl-4-(2-phthalimidethyl)-1-[2'-(1-trityl-1H-tetrazol-5-yl)biphenyl-4-yl]methylimidazole (10.69 g) as a white foam, characterized as its fumarate.

m.p. 173°–174° C.

NMR (DMSO-d₆)δ: 0.92 (3H, t), 2.35 (2H, q), 2.73 (2H, t), 3.78 (2H, t), 4.99 (2H, s)

REFERENCE EXAMPLE 15

To a solution of the above product (10.69 g) in ethanol (150 ml) and tetrahydrofuran (90 ml) at 0° C. is added hydrazine hydrate (6.25 g). The reaction mixture is stirred overnight at room temperature, filtered through a celite pad and evaporated. The residue is treated with 0.5N sodium hydroxide solution (300 ml) and extracted with chloroform. The organic layer is dried over sodium sulfate and concentrated to give the crude 2-ethyl-4-(2-aminoethyl)-1-[2'-(1-trityl-1H-tetrazol-5-yl)biphenyl-4-yl]methylimidazole (7.48 g) as a foam. This product is used without further purification.

REFERENCE EXAMPLE 16

To a solution of 2-ethyl-4-(2-phthalimidethyl)imidazole (9.00 g) and 2'-(t-butoxycarbonyl)biphenyl-4-yl-methyl bromide (13.93 g) in tetrahydrofuran (150 ml) and dimethylformamide (100 ml) at −60° C. is added potassium t-butoxide (4.12 g). The reaction mixture is allowed to slowly warm to room temperature in four hours and then poured into water (100 ml). Tetrahydrofuran is removed under reduced pressure and the aqueous layer is extracted with ethyl acetate. The organic layer is washed with brine, dried over sodium sulfate and then evaporated to give an oily residue. Purification by silica gel column chromatography (solvent; hexane/ethyl acetate) gives 2-ethyl-4-(2-phthalimidethyl)-1-[2'-(t-butylcarbonyl)biphenyl-4-yl]methylimidazole (9.39 g) as an oil.

NMR (CDCl₃)δ: 1.20 (3H, t), 1.25 (9H, s), 5.02 (2H, s), 6.64 (1H, s)

REFERENCE EXAMPLE 17

The compound obtained in Reference Example 16 is treated in the same manner as in Reference Example 15 to give 2-ethyl-4-(2-aminoethyl)-1-[2'-(t-butoxycarbonyl)-biphenyl-4-yl]methylimidazole.

FAB-MS (m/z): 406 (M+1), 211 (base)

NMR (CDCl₃)δ: 1.26 (9H, s), 1.29 (3H, t), 5.06 (2H, s), 6.60.(1H, s)

REFERENCE EXAMPLE 18

2-n-Butyl-1-dimethylsulfamoylimidazole (46.0 g) is treated in the same manner as in Reference Example 12 to give 2-n-butyl-1-dimethylsulfamoyl-5-[2'-(t-butoxycarbonyl)aminoethyl]imidazole (69 g) as an oil.

NMR (CDCl₃)δ: 0.95 (3H, t), 1.43 (9H, s), 2.86 (6H, s)

REFERENCE EXAMPLE 19

2-n-Butyl-1-dimethylsulfamoyl-5-[2'-(t-butoxycarbonyl)aminoethyl]imidazole (115.3 g) is treated in the same manner as in Reference Example 15 to give 2-n-butyl-4-(2-phthalimidethyl)imidazole (64 g).

m.p. 114°–117° C.

NMR (CDCl₃)δ: 0.88 (3H, t), 2.66 (2H, t), 2.97 (2H, t), 3.95 (2H, t), 6.67 (1H, s)

REFERENCE EXAMPLE 20

The compound obtained in Reference Example 19 is treated in the same manner as in Reference Example 14 to give 2-n-butyl-1-[2'-(1-trityl-1H-tetrazol-5-yl)biphenyl-4 -yl]methyl-4-(2-phthalimidethyl)imidazole.

NMR (CDCl₃)δ: 0.84 (3H, t), 4.81 (2H, s)

REFERENCE EXAMPLE 21

A mixture of 2-n-butyl-4-(2-phthalimidethyl)-1-[2'-(1-trityl-1H-tetrazol-5-yl)biphenyl-4-yl]methylimidazole (96.0 g), hydrazine hydrate (44.7 g) and ethanol (1.3 liter) is stirred overnight at room temperature, then filtered through a celite pad and evaporated. The residue is treated with 5% sodium hydroxide solution (200 ml) and extracted with chloroform. The organic layer is dried and concentrated to give the crude 2-n-butyl-4-(2-aminoethyl)-1-[2'-(1-trityl-1H-tetrazol-5-yl)biphenyl-4-yl]methylimidazole (84.0 g). To a solution of the above product (84.0 g) in methanol is added a 24% hydrogen chloride methanol solution (200 ml), and the mixture is evaporated. To the residue is added water (2 liters), and the mixture is washed with ether. The aqueous layer is concentrated to give 2-n-butyl-4-(2-aminoethyl)-1-[2'-(1-tetrazol-5-yl)biphenyl-4-yl]methylimidazole dihydrochloride (52.8 g) as a foam.

NMR (DMSO-d₆)δ: 0.83 (3H, t), 2.92 (2H, t), 5.41 (2H, s)

REFERENCE EXAMPLE 22

2-n-Propyl-1-dimethylsulfamoylimidazole (20.0 g) is treated in the same manner as in Reference Example 12 to give 2-n-propyl-1-dimethylsulfamoyl-5-(2-t-butoxycarbonylaminoethyl)imidazole (24.4 g) as an oil.

NMR (CDCl₃)δ: 1.01 (3H, t), 1.43 (9H, s), 2.86 (6H, s), 6.71 (1H, s)

REFERENCE EXAMPLE 23

The compound obtained in Reference Example 22 is treated in the same manner as in Reference Example 15 to give 2-n-propyl-4-(2-phthalimidethyl)imidazole.

m.p. 137°–139° C.

NMR (CDCl₃)δ: 0.90 (3H, t), 3.95 (2H, t), 6.68 (1H, s)

REFERENCE EXAMPLE 24

To a mixture of 2-n-propyl-4-(2-phthalimidethyl)imidazole (10.0 g), 2'-(t-butoxycarbonyl)biphenyl-4-ylmethyl bromide (13.5 g), tetrahydrofuran (150 ml) and dimethylformamide (15 ml) is added a solution of potassium t-butoxide (4.16 g) in tetrahydrofuran (40 ml) at −60° C. The mixture is allowed to warm to room temperature, and then quenched with water. The mixture is extracted with ethyl acetate, and the organic layer is washed, dried and evaporated. The crude product is crystallized with oxalic acid from ethanol/ether to give 2-n-propyl-4-(2-phthalimidethyl)-1-[2'-(t-butoxycarbonyl)biphenyl-4-yl]methylimidazoleoxalate (15.6 g).

m.p. 128°–131° C.

NMR (DMSO-d₆)δ: 0.84 (3H, t), 1.19 (9H, s), 5.30 (2H, s)

REFERENCE EXAMPLE 25

To a mixture of 2-n-propyl-4-(2-phthalimidethyl)-1-[2'-(tert-butoxycarbonyl)bipheyl-4-yl]methylimidazole (15.5 g) and ethanol (150 ml) is added hydrazine hydrate (8.45 g) at room temperature. The mixture is stirred overnight, and the precipitate is removed by filtration. The filtrate is evaporated, and the resulting residue is dissolved in chloroform and washed with 3% sodium hydroxide solution and brine. The organic layer is dried and evaporated to give the crude 2-n-propyl-4-aminoethyl-1-[2'-(tert-butoxycarbonyl)biphenyl-4-yl]methylimidazole (10.0 g). This compound is used in the next step without further purification.

EFFECTS OF THE INVENTION

The imidazopyridine derivatives [I] of the present invention and pharmaceutically acceptable salts thereof show excellent angiotensin II antagonistic activities and are useful in the prophylaxis and/or treatment of hypertension. For example, when hypotensive activity was examined by using spontaneously hypertensive rats orally administered at a dose of 3 mg/kg of the desired compounds [I] of the present invention, significant hypotensive activity was observed as compared with that of the control group of rats to which purified water is orally administered. Moreover, the compounds [I] of the present invention and pharmaceutically acceptable salts thereof show low toxicity, and hence, they show high safety as a medicament.

What is claimed is:

1. An imidazopyridine derivative of the formula (I):

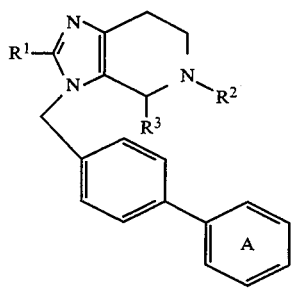

[I]

wherein $R^1$ is a lower alkyl group; $R^2$ is a group of the formula

in which Z is an oxygen atom and $R^0$ is a lower alkyl group; $R^3$ is a carboxyl group or a lower alkoxy-carbonyl group; and Ring A is a tetrazolyl-substituted phenyl group, or a pharmaceutically acceptable salt thereof.

2. The compound according to claim 1, wherein $R^3$ is a carboxyl group.

3. A pharmaceutical composition which comprises a therapeutically effective amount of the compound as set forth in claim 1 in admixture with a conventional pharmaceutically acceptable carrier or diluent.

4. A method for the prophylaxis or treatment of hypertension which comprises administering to a warm-blooded animal a therapeutically effective amount of the compound as set forth in claim 1.

5. 2-n-Propyl-5-acetyl-3-[2'-(1H-tetrazol-5-yl)biphenyl-4yl[methyl-4,5,6,7-tetrahydroimidazo[4,5-c]-pyridine-4-carboxylic acid or a pharmaceutically acceptable salt thereof.

6. A method for the prophylaxis or treatment of hypertension which comprises administering to a warm-blooded animal a therapeutically effective amount of the compound as set forth in claim 5.

7. 2-n-Butyl-5-acetyl-3-[2'-(1H-tetrazol-5-yl)-biphenyl-4-yl]methyl-4,5,6,7-tetrahydroimidazo[4,5-c]-pyridine-4-carboxylic acid or a pharmaceutically acceptable salt thereof.

8. A method for the prophylaxis or treatment of hypertension which comprises administering to a warm-blooded animal a therapeutically effective amount of the compound as set forth in claim 7.

9. 2-n-Butyl-5-propionyl-3-[2'-(1H-tetrazol-5-yl)biphenyl-4-yl]methyl-4,5,6,7-tetrahydroimidazo[4,5-c]-pyridine-4-carboxylic acid and a pharmaceutically acceptable salt thereof.

10. A method for the prophylaxis or treatment of hypertension which comprises administering to a warm-blooded animal a therapeutically effective amount of the compound as set forth in claim 9.

* * * * *